(12) United States Patent
Heiss et al.

(10) Patent No.: US 7,045,361 B2
(45) Date of Patent: May 16, 2006

(54) ANALYTE SENSING VIA ACRIDINE-BASED BORONATE BIOSENSORS

(75) Inventors: Aaron M. Heiss, Sherman Oaks, CA (US); Joseph C. Walsh, Los Angeles, CA (US); David J. Vachon, Granada Hills, CA (US); Glenn Noronha, Oceanside, CA (US); Jonathan Reilly, Reseda, CA (US); Bill C. Ponder, Fort Worth, TX (US); William P. Van Antwerp, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 235 days.

(21) Appl. No.: 09/952,563

(22) Filed: Sep. 12, 2001

(65) Prior Publication Data

US 2005/0191761 A1    Sep. 1, 2005

(51) Int. Cl.
G01N 21/64 (2006.01)
G01N 33/58 (2006.01)
G01N 33/66 (2006.01)

(52) U.S. Cl. .......................... 436/172; 436/95; 436/501

(58) Field of Classification Search ................ 436/531, 436/546, 172, 501, 95; 546/102, 105, 106, 546/113
See application file for complete search history.

(56) References Cited

U.S. PATENT DOCUMENTS

| | | | |
|---|---|---|---|
| 4,236,071 A | 11/1980 | Chimenti |
| 4,401,122 A | 8/1983 | Clark, Jr. |
| 4,428,366 A | 1/1984 | Findl et al. |
| 4,455,741 A | 6/1984 | Kolodner |
| 4,496,722 A | 1/1985 | Gallop et al. |
| 4,542,987 A | 9/1985 | Hirschfeld |
| 4,600,306 A | 7/1986 | Hara et al. |
| 4,655,225 A | 4/1987 | Dahne et al. |
| 4,680,268 A | 7/1987 | Clark, Jr. |
| 4,805,623 A | 2/1989 | Jobsis |
| 4,861,728 A | 8/1989 | Wagner |
| 4,875,486 A | 10/1989 | Rapoport et al. |
| 4,882,492 A | 11/1989 | Schlager |
| 4,923,819 A | 5/1990 | Fernandez et al. |
| 4,924,009 A | 5/1990 | Neckers et al. |
| 4,929,387 A | 5/1990 | Hayden et al. |
| 4,974,929 A | 12/1990 | Curry |
| 5,028,787 A | 7/1991 | Rosenthal et al. |
| 5,032,315 A | 7/1991 | Hayden et al. |
| 5,049,738 A | 9/1991 | Gergely et al. |
| 5,054,487 A | 10/1991 | Clarke |
| 5,070,874 A | 12/1991 | Barnes et al. |
| 5,077,476 A | 12/1991 | Rosenthal |
| 5,086,229 A | 2/1992 | Rosenthal et al. |
| 5,101,814 A | 4/1992 | Palti |
| 5,112,124 A | 5/1992 | Harjunmaa et al. |
| 5,137,833 A | 8/1992 | Russell |
| 5,173,456 A | 12/1992 | Hayden et al. |
| 5,182,214 A | 1/1993 | Kessler et al. |
| 5,196,709 A | 3/1993 | Berndt et al. |
| 5,198,670 A | 3/1993 | VanCauter et al. |
| 5,203,328 A | 4/1993 | Samuels et al. |
| 5,235,045 A | 8/1993 | Lewis et al. |
| 5,235,606 A | 8/1993 | Mourou et al. |
| 5,246,867 A | 9/1993 | Lakowicz et al. |
| 5,262,526 A | 11/1993 | Sassamoto et al. |
| 5,270,548 A | 12/1993 | Steinkamp |
| 5,279,543 A | 1/1994 | Glikfeld et al. |
| 5,281,825 A | 1/1994 | Berndt et al. |
| 5,308,773 A | 5/1994 | Lewis et al. |
| 5,313,485 A | 5/1994 | Hamil et al. |
| 5,322,796 A | 6/1994 | Ishikawa |
| 5,342,789 A | 8/1994 | Chick et al. |
| 5,353,790 A | 10/1994 | Jacques et al. |
| 5,362,307 A | 11/1994 | Guy et al. |
| 5,409,835 A | 4/1995 | Lakowicz et al. |
| 5,439,797 A | 8/1995 | Tsien et al. |

(Continued)

FOREIGN PATENT DOCUMENTS

EP    0 673 622 A3    9/1995

(Continued)

OTHER PUBLICATIONS

Appleton et al., "Detection of Total Sugar Concentration Using Photoinduced Electron Transfer Materials: Development of Operationally Stable, Reusable Optical Sensors," Sensors and Actuators B, Elsevier Sequoia, 2000, 65(1-3): 302-304.

(Continued)

Primary Examiner—Mary E. Ceperley
(74) Attorney, Agent, or Firm—Gates & Cooper LLP

(57) ABSTRACT

Fluorescent biosensor molecules, fluorescent biosensors and systems, as well as methods of making and using these biosensor molecules and systems are described. These biosensor molecules address the problem of obtaining fluorescence emission at wavelengths greater than about 500 nm. Biosensor molecules generally include an (1) an acridine-based fluorophore, (2) a linker moiety and (3) a boronate substrate recognition/binding moiety, which binds polyhydroxylate analytes, such as glucose. These biosensor molecules further include a "switch" element that is drawn from the electronic interactions among these submolecular components. This fluorescent switch is generally "off" in the absence of bound polyhydroxylate analyte and is generally "on" in the presence of bound polyhydroxylate analyte. Thus, the reversible binding of a polyhydroxylate analyte essentially turns the fluorescent switch "on" and "off". This property of the biosensor molecules, as well as their ability to emit fluorescent light at greater than about 500 nm, renders these biosensor molecules particularly well-suited for detecting and measuring in-vivo glucose concentrations.

21 Claims, 18 Drawing Sheets

U.S. PATENT DOCUMENTS

| | | | |
|---|---|---|---|
| 5,445,611 A | 8/1995 | Eppstein et al. |
| 5,458,140 A | 10/1995 | Eppstein et al. |
| 5,476,094 A | 12/1995 | Allen et al. |
| 5,485,530 A | 1/1996 | Lakowicz et al. |
| 5,495,850 A | 3/1996 | Zuckerman |
| 5,503,770 A | 4/1996 | James et al. |
| 5,504,337 A | 4/1996 | Lakowicz et al. |
| 5,512,246 A | 4/1996 | Russell et al. |
| 5,515,864 A | 5/1996 | Zuckerman |
| 5,528,046 A | 6/1996 | Ishikawa |
| 5,528,611 A | 6/1996 | Scheps |
| 5,590,141 A | 12/1996 | Baird et al. |
| 5,599,504 A | 2/1997 | Hosoi et al. |
| 5,626,134 A | 5/1997 | Zuckerman |
| 5,628,310 A | 5/1997 | Rao et al. |
| 5,648,270 A | 7/1997 | Kuhn et al. |
| 5,666,373 A | 9/1997 | Sharp et al. |
| 5,674,743 A | 10/1997 | Ulmer |
| 5,763,238 A | 6/1998 | James et al. |
| 5,776,782 A | 7/1998 | Tsuji |
| 5,784,157 A | 7/1998 | Gorfinkel et al. |
| 5,798,306 A | 8/1998 | Dickinson, Jr. |
| 5,814,820 A | 9/1998 | Dong et al. |
| 5,818,582 A | 10/1998 | Fernandez et al. |
| 5,825,798 A | 10/1998 | Momiuchi et al. |
| 5,846,726 A | 12/1998 | Nadeau et al. |
| 5,865,754 A | 2/1999 | Sevick-Muraca et al. |
| 5,888,739 A | 3/1999 | Pitner et al. |
| 5,909,278 A | 6/1999 | Deka et al. |
| 5,911,952 A | 6/1999 | Tsuji |
| 5,919,630 A | 7/1999 | Nadeau et al. |
| 5,928,869 A | 7/1999 | Nadeau et al. |
| 5,935,791 A | 8/1999 | Nadeau et al. |
| 5,952,236 A | 9/1999 | Thompson et al. |
| 5,955,737 A | 9/1999 | Hallidy et al. |
| 5,981,957 A | 11/1999 | Cruce et al. |
| 5,987,049 A | 11/1999 | Weingarten et al. |
| 5,990,484 A | 11/1999 | Ohsuka |
| 5,994,707 A | 11/1999 | Mendoza et al. |
| 6,002,954 A | 12/1999 | Van Antwerp et al. |
| 6,011,984 A | 1/2000 | Van Antwerp et al. |
| 6,040,194 A | 3/2000 | Chick et al. |
| 6,157,037 A | 12/2000 | Danielson |
| 6,184,535 B1 | 2/2001 | Kashima et al. |
| 6,200,818 B1 | 3/2001 | Eigen et al. |
| 6,214,628 B1 | 4/2001 | Lakowicz et al. |
| 6,225,127 B1 | 5/2001 | Thompson et al. |
| 6,344,360 B1 | 2/2002 | Colvin et al. |

FOREIGN PATENT DOCUMENTS

| | | |
|---|---|---|
| EP | 0 693 271 A1 | 1/1996 |
| EP | 0729 962 A1 | 9/1996 |
| FR | 2 253 794 | 7/1975 |
| GB | 2 284 809 | 6/1995 |
| WO | WO 82/01804 | 5/1982 |
| WO | WO 91/04488 | 4/1991 |
| WO | WO 91/18912 | 12/1991 |
| WO | WO 96/03074 | 2/1996 |
| WO | WO 97/19188 | 5/1997 |
| WO | WO 97/29154 | 8/1997 |
| WO | WO 98/22820 | 5/1998 |
| WO | WO 99/46600 | 9/1999 |
| WO | WO 01/18543 | 3/2001 |
| WO | WO 01/20334 | 3/2001 |
| WO | WO 02/054067 | 7/2002 |

OTHER PUBLICATIONS

Arnold et al., "Determination of Physiological Levels . . . Spectra," Anal. Chem., 1990, 62:1457-1464.

Bostick et al., "Quantitative Determination of Blood . . . Luminol," Anal. Chemistry, 1975, 47(3):447-452.

Burnett et al., "Synthesis of a Fluorescent Boronic Acid . . . Erythrocytes," Biochemical and Biophysical Research Communications, 1980, 96(1): 157-162.

Czarnik, "Chemical Communication in . . . Chemosensors," Acc. Chem. Res., 1994, 27:302-308.

DCCT Research Group, "The Effect of Intensive Treatment . . . Mellitus," The New England Journal of Medicine, 1993, 329(14):977-986.

Falasca et al., "Purification and Partial . . . Sativa," Biochimica et Biophysica Acta, 1979, 577:71-81.

Gough et al., "Development of the Implantable Glucose Sensor," Diabetes, 1995, 44:1005-1009.

Guilbault et al., "Homovanillic Acid as a . . . Enzymes," Analytic Chemistry, 1968, 40(1):190-196.

Indelli et al., "Salt Effects in the Reaction . . . Ions," Journal of the American Chemical Society, 1960, 82(13):3233, 3863-3866.

James et al., "Novel Photoinduced . . . Amine," J. Chem. Soc., Chem. Commun., 1994, pp. 477-478.

James, et al., "Novel Saccharide-Photoinduced . . . Amine," J. Am. Chem. Soc., 1995, 117:8982-8987.

James et al., "Chiral discrimination of . . . sensor," Nature, 1995, 374:345-347.

Joon et al., "Fluorescent chemosensors . . . found," SPIE, 1992, vol. 1796, pp. 87-91.

Lakowicz, et al., "Emerging Biomedical and Advanced Applications . . . Spectroscopy," Journal of Fluorescence, 1994, 4(1):117-136.

Lakowicz et al., "Fluorescence lifetime-based sensing . . . glucose," Sensors and Actuators B, 1993, 11:133-143.

Lin et al., J. Org. Chem., 1979, 44(25):4701-4703.

Kemp et al., "Synthesis of Cyclophanes . . . methylnaphthalenes," The Journal of Organic Chemistry, 1979, 44(25):4700-4703.

Marquardt et al., "Near-Infrared Spectroscopic . . . Matrix," Anal. Chem., 1993, 65:3271-3278.

Mohler et al., "α-Amino Acid Chelative . . . Acid," J. Am. Chem. Soc., 1993, 115:7037-7038.

Monroe, "Novel implantable glucose sensors," ACL, 1989, pp. 8-16.

Nakashima et al., "Sugar-Assisted Chirality . . . Complexes," Chemistry Letters, 1994, pp. 1267-1270.

Okafor, "Synthesis, Properties and Uses of Angular Phenoxazines," Dyes and Pigments, Elsevier Applied Science Publishers Ltd., England, vol. 7, No. 2, 1986, pp. 103-131, XP-002122264.

Patterson et al., "Tuning the Affinity of a Synthetic Sialic Acid Receptor Using Combinatorial Chemistry," Tetrahedron Lett., 1998, 39(20): 3111-3114.

Pilosof et al., "Microporous Membrane Flow . . . Glucose," Anal. Chem., 1982, 54:1698-1701.

Reach et al., Anal. Chem., 1992, 64(6):381-386.

Sandanayake et al., "Molecular Fluorescence Sensor . . . Coumarin," Chemistry Letters, 1995, pp. 139-140.

Uziel et al., "Direct Labeling of DNA . . . Group," Biochemical and Biophysical Research Communications, 1991, 180(3):1233-1240.

Xuhong, Qian et al., "The Synthesis, Application and Prediction of Stokes Shift in Fluorescent Dyes Derived from 1,8-Naphthalic Anhydride," Dyes and Pigments, Elsevier Applied Science Publishers Ltd., England, vol. 11, No. 1, 1989, pp. 13-20, XP-000026521.

Yoon et al., "Fluorescent chemosensors . . . found[1]," SPIE, 1992, 1796:87-91.

Yoon et al., "Fluorescent Chemosensors of . . . Quenching[1]," J. Am. Chem. Soc. 1992, 114:5874-5875.

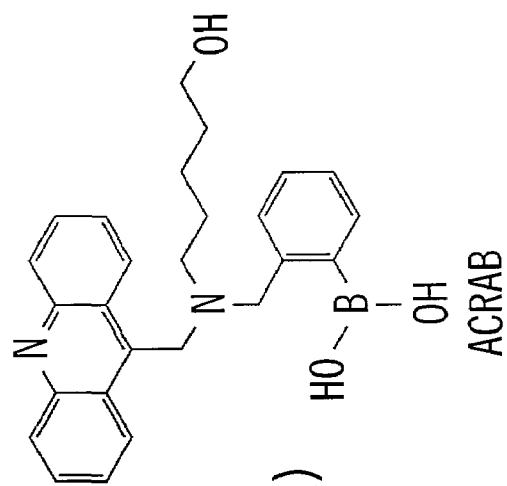
FIG. 3(a) ACRAB
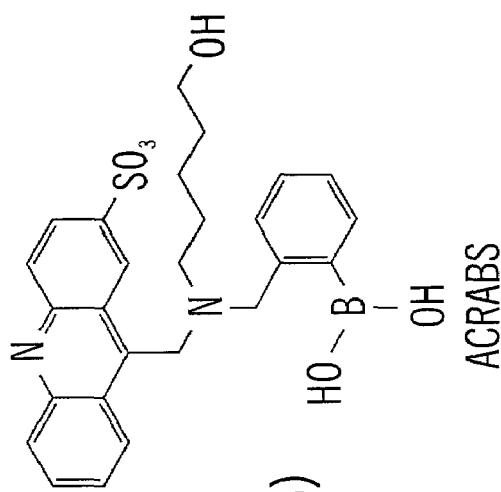
FIG. 3(b) ACRABS
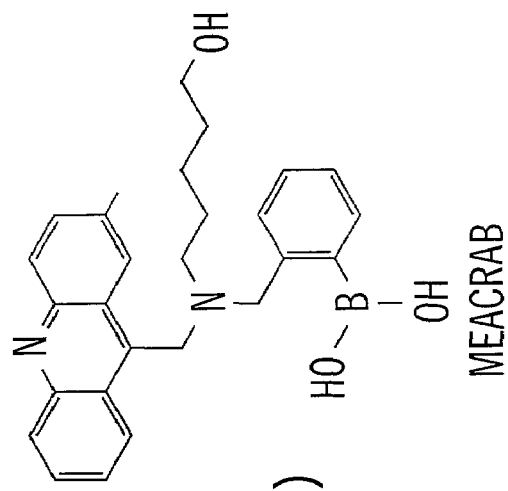
FIG. 3(c) MEACRAB
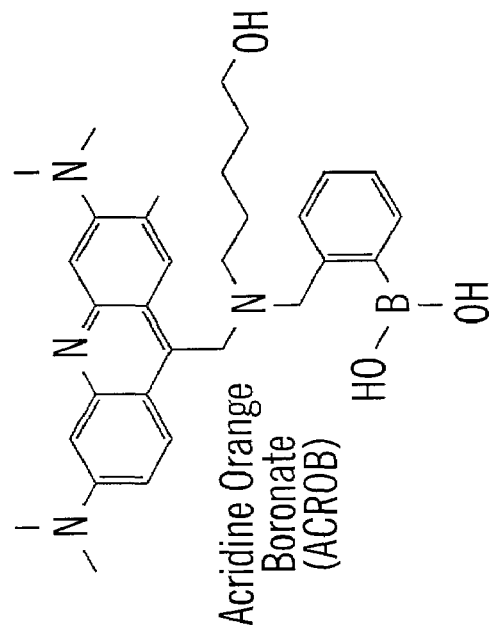
FIG. 3(d) Acridine Orange Boronate (ACROB)

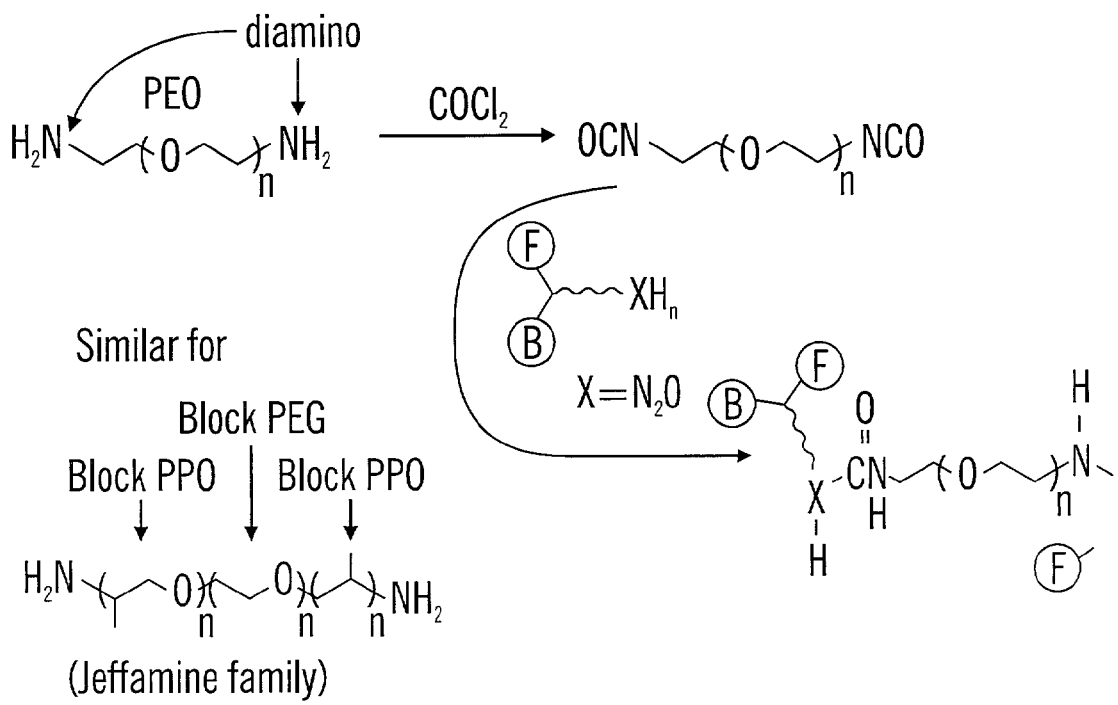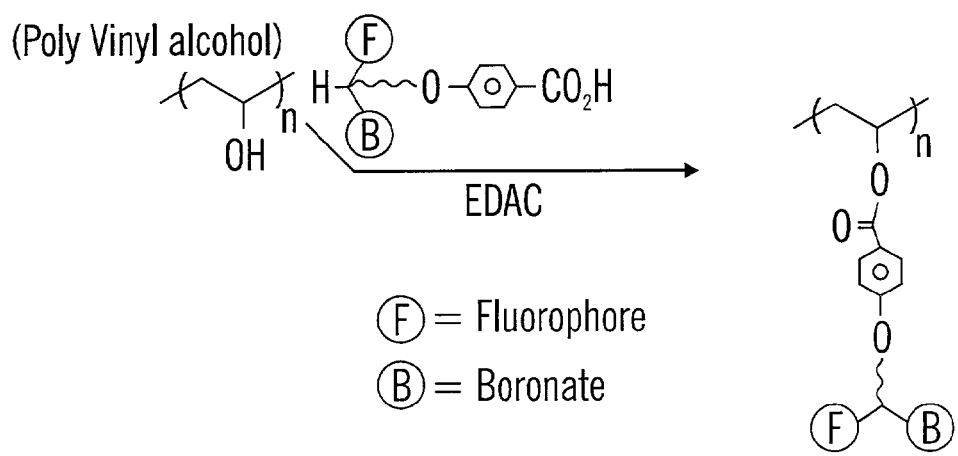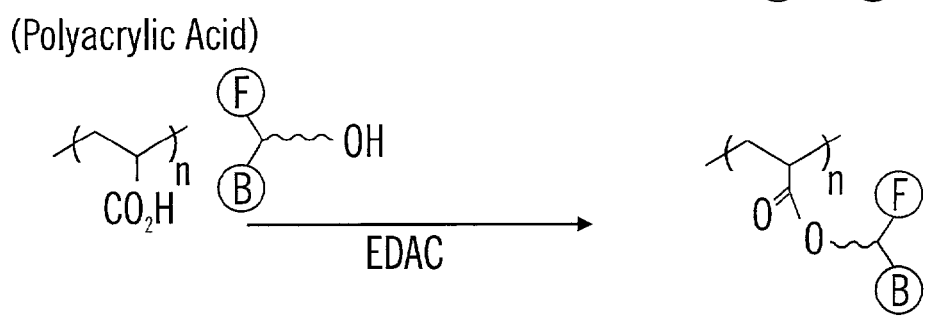
FIG. 15

ANALYTE SENSING VIA ACRIDINE-BASED BORONATE BIOSENSORS

This invention was made with the United States Government support under CRADA No. 70NANB8H4065 awarded by the National Institute of Standards and Technology (NIST). The United Stated Government has certain rights in the invention.

FIELD OF THE INVENTION

This invention relates to optical biosensor systems that utilize acridine-based boronate biosensor molecules for determination of the concentration of polyhydroxlate analytes, particularly glucose. More specifically, the invention relates to implantable, optical biosensor systems that utilize an acridine-based boronate biosensor system for the determination of in-vivo glucose concentrations.

BACKGROUND OF THE INVENTION

The accurate detection of in-vivo glucose concentrations is essential to the treatment and care of the diabetic patient. Current technology generally requires that a blood sample be obtained from a patient for the measurement of blood glucose levels. In order to accurately reflect the body's ever-changing response to meals, activities and even stress, measurement of blood glucose should be on a frequent basis. Due to the a discomfort and biohazard issues, the frequent sampling of a patient's blood to determine glucose levels is impractical, at best. Thus, devices and methods to frequently monitor blood glucose levels without taking numerous blood samples from a patient are desirable.

Fluorescent reporter molecules may be useful in monitoring changing glucose levels in-vivo. However, in order to use fluorescent reporter molecules to detect and measure the concentration of glucose in-vivo, numerous problems need to be surmounted. One particular problem is that fluorescence transmitted through skin is generally poor at visible wavelengths less than about 500 nm. Furthermore, at wavelengths less than about 500 nm, there is an additional problem of background autofluorescence from tissue which decreases the signal to noise ratio of the transmitted fluorescent signal.

Embodiments of this invention address the problem of obtaining adequate optical transmission of fluorescence using fluorescent reporter molecules in-vivo to report on the body's fluctuating glucose concentrations.

SUMMARY OF THE DISCLOSURE

Embodiments of the biosensor molecules of the present invention include an acridine-based fluorophore, a boronate binding moiety which specifically binds polyhydroxlate analyte, and a linker moiety which provides a linkage between the fluorophore and the boronate binding moiety. These biosensor molecules emit light in the visible region of the spectrum, preferably above about 500 nm.

Additionally, embodiments of the biosensor molecules of the invention have at least one maximum wavelength in their emission spectra that is greater than about 420 nm, more preferably above about 500 nm. Further, these biosensor molecules have at least one wavelength in their emission spectra that is greater than about 450 nm and exhibits an intensity that is at least about 25 percent of the intensity of a wavelength of maximum intensity in the visible region of the spectrum, more preferably these biosensor molecules have at least one wavelength in their emission spectrum that is greater than about 550 nm and exhibits an intensity that is at least 25 percent of the intensity of a wavelength of maximum intensity in the visible region.

An exemplary acridine-based boronate biosensor molecule of the present invention utilizes acridine orange as the fluorophore. The acridine orange-based boronate biosensor molecule has an excitation wavelength of about 500 nm and a maximum emission wavelength of about 530 nm. This acridine orange-based boronate biosensor molecule also exhibits approximately 50 percent of the intensity of this wavelength of maximum intensity at about 570 nm. However, other acridine-based fluorophores suitable for use in embodiments of the present invention may include one or more functional groups selected from the following: aliphatic, aromatic, haloalkane, alcohol, ether, amine, cyano, nitro group, aldehyde, ketone, ester, carboxylic acid, sulfonic acid and phosphoric acid functional groups.

Other embodiments of the acridine-based boronate biosensor molecules of the invention include ditopic molecules, which generally include two boronate substrate recognition sites. These ditopic embodiments of the invention are capable of binding to one or more polyhydroxylate analyte molecules, such as glucose, per ditopic biosensor molecule, and thus, increase the sensitivity of the sensing ability of these biosensor molecules.

Generally for in-vivo measurements of polyhydroxylate analytes, particularly for glucose measurements, these acridine-based boronate biosensor molecules are either contained within, or attached to, a polymer matrix to form embodiments of the fluorescent biosensor of the invention. Preferably, the polymer matrix materials selected for use with the biosensors of the invention are biocompatible. The use of biocompatible polymeric materials is especially preferred for surfaces of the biosensor that are to be in contact with body fluids and tissue. Thus, embodiments of the biosensors of the invention are especially suitable for implantation beneath the skin where they serve as in-vivo reporters of analyte concentrations, particularly glucose concentrations.

Other aspects of the invention include methods for preparing an acridine-based biosensor molecule. These methods generally include the following steps. First an acridine-based fluorophore with the following general structure is chosen:

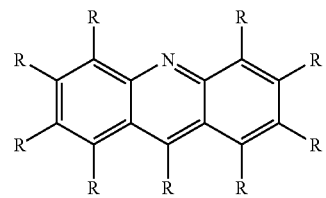

where N is nitrogen and each R group is independent and is selected from the group consisting of substituents which alter the electronic properties of the acridine-based fluorophore, functional groups that are capable of forming covalent linkages to a linker moiety, to a bridging linker element, to a polymer matrix. Next a linker moiety is selected that includes from about 4 to about 10 atoms, selected from carbon, nitrogen, oxygen or sulfur, but preferably carbon atoms, and at least two functional groups that can react to form covalent linkages, one functional group being capable of reacting to form a covalent linkage to an R group on the acridine-based fluorophore and one functional group capable of reacting to form a covalent linkage to a polymer matrix. Finally, a polyhydroxylate binding moiety with the following general structure is selected:

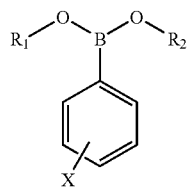

where X is located at any position on the phenyl group. Further, there can be more than one X functional group. One or more of these X groups may be capable of reacting with a functional group on the linker moiety to yield covalent linkages. $R_1$ and $R_2$ are hydrogen or aliphatic groups consisting of 1–10 carbons and are either the same group, different groups or linked to form one group. The three components of the acridine-based boronate bio sensor molecules in accordance with embodiments of the invention then are reacted to yield the bio sensor molecules in accordance with embodiments of the invention by forming covalent linkages between the fluorophore and the linker moiety and between the linker moiety and the substrate recognition/binding moiety In particular embodiments of the above synthetic method, the functional group on the acridine-based fluorophore that is capable of forming a covalent linkage to the linker moiety is an aldehyde, an amine or a halogen. Also in embodiments of the synthetic method, the linker moiety includes an amino functional group. Still other embodiments of this general method include reacting a linker moiety that further includes a hydroxyl, an amino or a carboxy functional group capable of forming a covalent attachment to a polymer matrix. Further, in particular embodiments, the phenyl group on the polyhydroxylate analyte binding moiety includes a reactive halogen.

Other aspects of the invention include an acridine-based boronate fluorescent biosensor systems for measuring in-vivo levels of a polyhydroxylate analyte, particularly glucose. Embodiments of these biosensor systems include an acridine-based fluorescent biosensor molecule attached to, or contained within, a polymer matrix to yield an acridine-based boronate biosensor of the biosensor system. These biosensor systems also include an optical light source and a detector that detects a fluorescent signal that can be correlated with in-vivo levels of the polyhydroxylate analyte.

Further, the embodiments of the biosensor system of the invention include a biosensor that is implanted subcutaneously beneath a person's skin. These biosensors may also include various agents that increase the overall biocompatibility and functioning of the biosensors when these agents are admixed into the polymer matrix, or coated atop of the polymer matrix that is in contact with the body, or the like. Particular embodiments of the biosensor system include an implanted biosensor that emits light through the skin of the person with this light being detected by the detector. Other embodiments include biosensor systems where the biosensor is transdermally, or percutaneously, implanted and includes a fiber optic for light passage through to, or from, the implanted biosensor. Biosensor systems in accordance with embodiments of the invention may be injected subcutaneously beneath a person's skin.

Another aspect of the invention are methods of quantifying the amount of polyhydroxylate analyte in-vivo, particularly glucose. These methods include interrogating an implanted acridine-based boronate biosensor, which includes acridine-based boronate biosensor molecules contained within or attached to a polymer matrix, with a light source to produce excited state biosensor molecules that yield an emission signal. This emission signal, which correlates to the amount of polyhydroxylate analyte in the body fluids surrounding the biosensor implant, is then detected by a detector. Finally the amount of polyhydroxylate analyte surrounding the in-vivo implanted biosensor is quantified from the emission signal. These methods preferably utilize biosensor molecules that have an emission signal at about 500 nm or greater, more preferably at about 600 nm.

More generally embodiments of the invention include acridine-based biosensor molecules that includes an acridine-like, three-ringed fluorophore with the following structure:

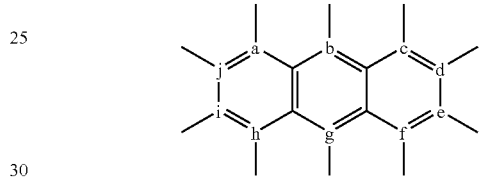

where the fluorophore includes at least one heteroatom selected from nitrogen, sulfur and oxygen at any position a–j, except that at least one position a–j does not include a heteroatom, and wherein the fluorophore includes at least one substituent selected from a methyl, ethyl, propyl, butyl, aldehyde, chloro and bromo groups that are attached at the position that does not include a heteroatom. These embodiments of the invention further include a boronate binding moiety which specifically and reversibly binds polyhydroxylate analyte and a linker moiety which links the fluorophore to the boronate binding moiety. Further, these biosensor molecules emit a signal in the visible to near infrared region of the spectrum that can be correlated to polyhydroxylate analyte concentration.

Still other aspects of the invention include an implantable biosensor which includes an acridine-based fluorophore; a boronate binding moiety which specifically and reversibly binds polyhydroxylate analyte; a linker moiety which links the fluorophore to the boronate binding moiety to form a biosensor molecule, where the biosensor molecule emits a signal in the visible to near infrared region of the spectrum that can be correlated to polyhydroxylate analyte concentration; and a polymer matrix that is attached to the biosensor molecules. The polymer matrix may be water-soluble and selected from at least polyethylene glycol (amino-terminated), Jeffamine polymers (2-propyl amino-terminated block-polypropylene oxide block-polyethylene oxide block-polypropylene oxide), poly(vinyl alcohol), poly(acrylic acid) and mixtures of these polymers. Using a water-soluble polymer matrix to immobilize the acridine-based biosensor molecules in accordance with embodiments of the invention, requires that the biosensor is further contained in a biocompatible, water-insoluble material that is permeable to the polyhydroxylate analyte, where the water-insoluble material is selected from at least polyesters of carbonic acid, poly(vinylchloride), polyamides, polychloroethers, poly(urethanes), poly(imides) and mixtures of these materials. Moreover, the implantable biosensor may be immobilized in a polymer matrix that has multiple attachment-points, such as cross-linked poly(vinyl alcohol), crosslinked poly(acrylic acid), star dendrimers and mixtures of these polymers. When using these polymers no further encapsulation is required. A particular embodiment of an implantable biosensor in accordance with embodiments of the invention utilizes a polycarboxystyrene polymer matrix. In this example, as well as other examples of polymer matrices, the polymer matrix can be made to be water-soluble or water-insoluble by adjusting the overall length as well as the level of crosslinking of the polymer.

BRIEF DESCRIPTION OF THE DRAWINGS

FIG. 3(a–d) illustrates several acridine-based boronate biosensor molecules in accordance with embodiments of the invention.

FIG. 15 depicts some preferred embodiments of acridine-based biosensor molecules attached to water-soluble polymer matrices.

DETAILED DESCRIPTION OF THE PREFERRED EMBODIMENTS

Figure 1:
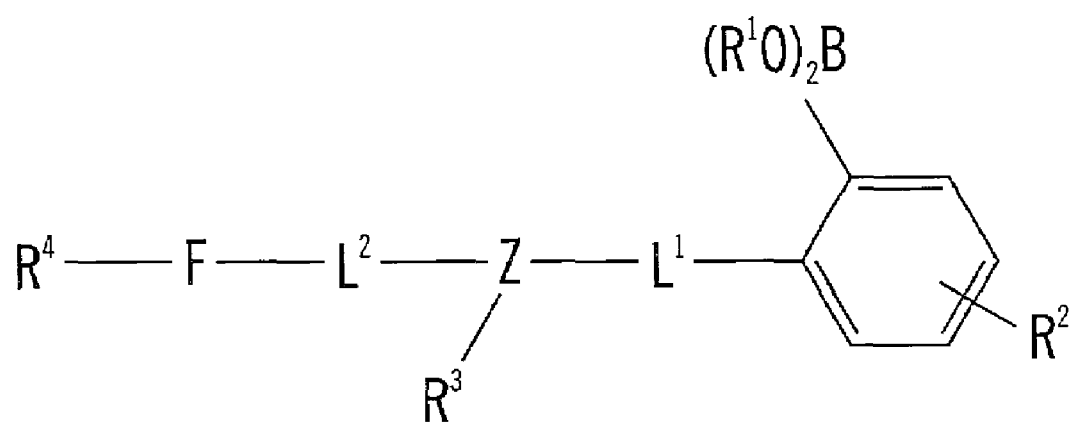
FIG. 1 shows a generalized acridine-based boronate biosensor molecule for use in embodiments of the invention where F is an acridine-based fluorophore.

Embodiments of the present invention are directed to fluorescent acridine-based boronate biosensor molecules, optical biosensor systems that include acridine-based boronate biosensor molecules encompassed within a polymer matrix, methods of making acridine-based biosensor molecules and methods of using these biosensor molecules to report on in-vivo levels of polyhydroxylate analytes. These biosensor molecules and systems are particularly useful for detection and measurement of in-vivo glucose concentrations via fluorescence. Related biosensor molecules and systems are described in U.S. Pat. No. 6,002,954, filed on Nov. 21, 1996, U.S. Ser. No. 09/663,567, filed on Sep. 15, 2001, U.S. Ser. No. 09/823,522, filed on Mar. 30, 2001, Ser. No. 09/826,745, filed on Apr. 4, 2001, and U.S. Provisional application Ser. No. 60/269,226, filed on Feb. 15, 2001, which are herein incorporated by reference in their entireties.

These acridine-based biosensor molecules in accordance with embodiments of the invention solve the problem of obtaining optimal optical transmission of fluorescence via implanted fluorescent reporter systems of in-vivo polyhydroxylate analyte concentrations. For example, embodiments of these biosensor molecules and systems exhibit wavelengths of fluorescence emission greater than about 450 nm, and accordingly, can be used to detect polyhydroxylate analytes, particularly glucose, in media with high opacities to visible light, such as human skin and tissue. These biosensor molecules and systems of the invention thus have the desired properties of long wavelengths of fluorescence emission, as well as exhibiting reasonably high quantum yields and high molar efficiencies. In addition, these biosensor molecules and systems generally exhibit excitation wavelengths greater than about 400 nm, and thus have the benefit of generally being excited at wavelengths that are above the ultraviolet range. Further, embodiments of the biosensor molecules of the invention have at least one maximum wavelength in their emission spectra that is greater than about 420 nm and have at least one wavelength in their emission spectra that is greater than about 450 nm and exhibits an intensity that is at least 25 percent of the intensity of a wavelength of maximum intensity in the visible region of the spectrum. Particular embodiments of the invention, however, may emit in the near infrared (IR) region of the spectrum.

A comparative analysis of the spectral properties of certain fluorophores is shown Table 1. The anthracene fluorophore is analogous to acridine, but does not contain a nitrogen atom in its central ring structure. However, as shown in Table 1, anthracene has no detectable emission at about 480 nm, whereas acridine exhibits an emission intensity at about 480 nm that is approximately 50% of the intensity of its maximum emission wavelength. This phenomenon is unexpected given the chemical similarity between anthracene and an acridine. As shown in the Table 1, the acridine orange fluorophore emits at even longer wavelengths.

TABLE 1

A Comparative Analysis of the Spectral Properties of the Anthracene, Acridine and Acridine Orange Fluorophores

| Fluorophore | $\lambda_{ex}$ (nm) | $\lambda_{em}$(max) (nm) | $\lambda_{em}$(50% max) (nm) |
|---|---|---|---|
| Anthracene | 370 | 417 | 428 |
| Acridine | 360 | 428 | 480 |
| Acridine Orange | 493 | 526 | 567 |

Measurements made in Phosphate Buffer Saline (PBS) containing 0.5% DMSO at 21° C. All measurements are within ±5%. "50% max" refers to a bathchromtic wavelength that is 50% of the wavelength of maximum absorbance in the visible region.

Figure 14A:
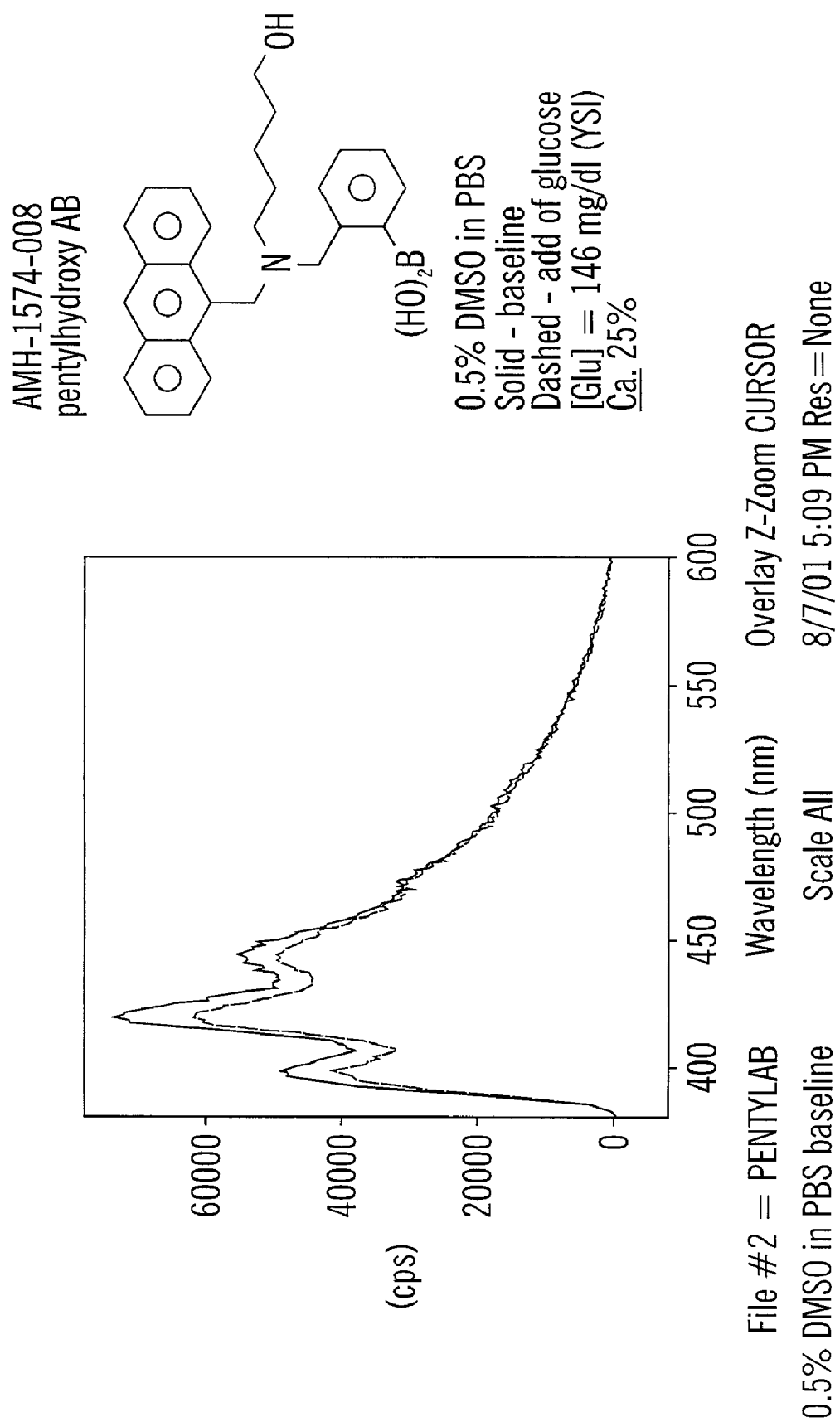
FIG. 14A depicts the results of a transduction experiment with anthracene boronate.
Figure 14B:
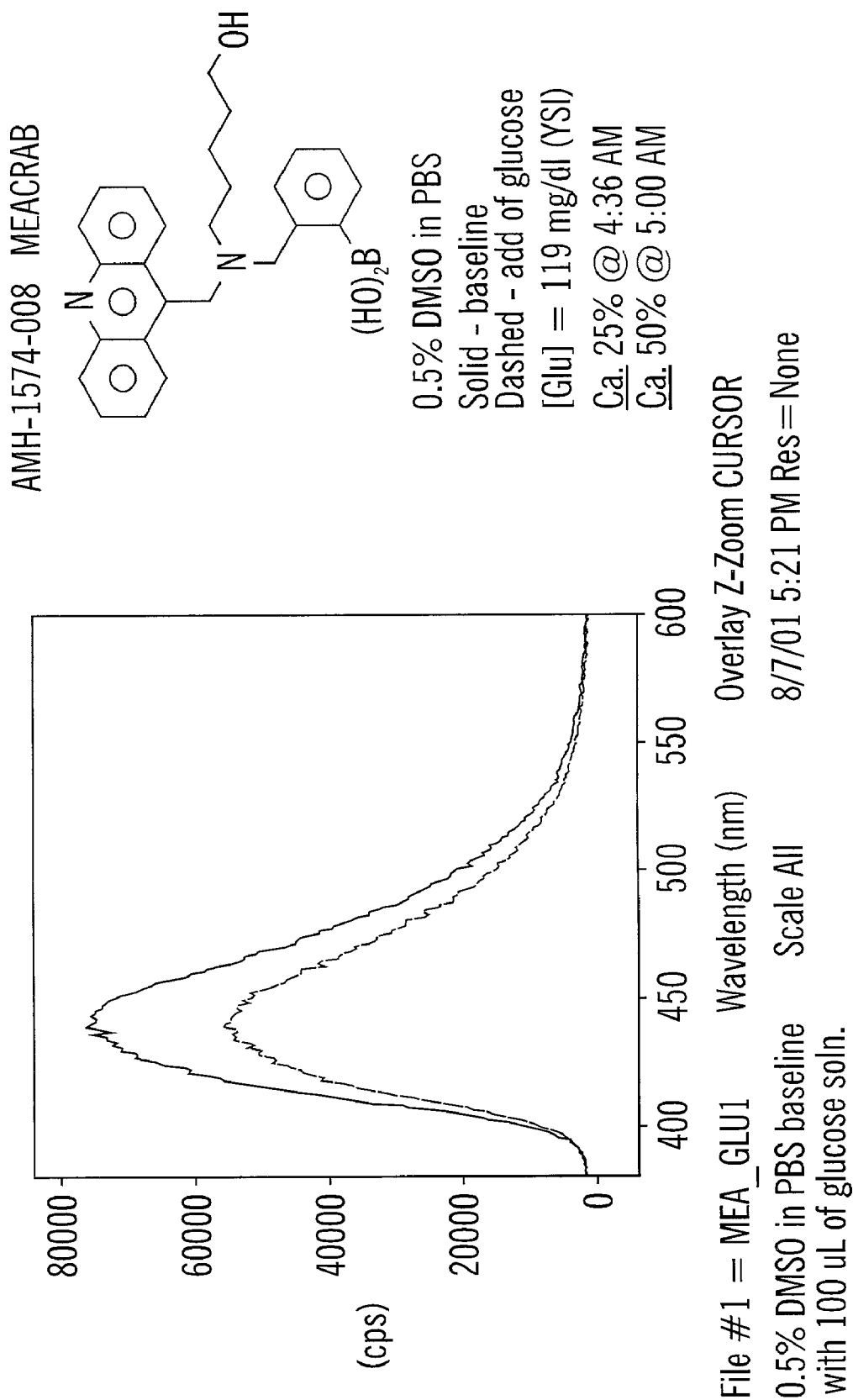
FIG. 14B depicts the results of a transduction experiment with methylacridine boronate (MEACRAB) in the presence of glucose.

A comparison of anthracene boronate and methylacridine boronate (MEACRAB) in the presence and absence of glucose further highlights the unexpected differences between these two fluorescent molecules in terms of their respective fluorescent properties, such as transduction of glucose at longer wavelengths, i.e., glucose sensing capacity as indicated by a change in fluorescence in the presence of glucose at longer wavelengths. These differences are illustrated in FIG. 14A and FIG. 14B, which depicts the emission spectra of anthracene boronate and methylacridine boronate, respectively in the presence and absence of glucose. From inspection of FIG. 14A, it can be observed that at about 440 nm, which is about at a peak of next to maximum intensity, anthracene boronate yields about 25% transduction in the presence of glucose. However, at wavelengths above about 460 nm, anthracene boronate is insensitive to the presence of glucose, as evidenced by the lack of any transduction at these wavelengths, i.e., a change in its fluorescence intensity in the presence of glucose over the baseline spectrum in the absence of glucose, at this wavelength or greater. On the other hand, as illustrated in FIG. 14B, methylacridine boronate, transduces about 50% at about 440 nm, but additionally, displays a significant ability to transduce in the presence of glucose at longer wavelengths. For instance, at about 500 nm, methylacridine boronate yields about 25% transduction in the presence of glucose. Thus, the ability of an acridine boronate, such as methylacridine boronate, to transduce in the presence of glucose at longer wavelengths, as compared with anthracene boronate, is unexpected. Moreover, the overall greater transduction ability of methylacridine boronate (FIG. 14A), as compared to the anthracene boronate (FIG. 14B), is especially unexpected since it would be predicted that the electron-donating ability of the nitrogen atom of the acridine fluorophore should yield a decrease in transduction ability of this biosensor molecule due to the photo-induced electron transfer (PET) properties of the resultant biosensor molecule being compromised by the inclusion of the aromatic heteroatom. See infra. Finally, another unknown and not necessarily expected property of the acridine-based boronate biosensor molecules in accordance with embodiments of the invention is the ability of these biosensor molecules to transduce glucose in aqueous solutions.

Figure 2:
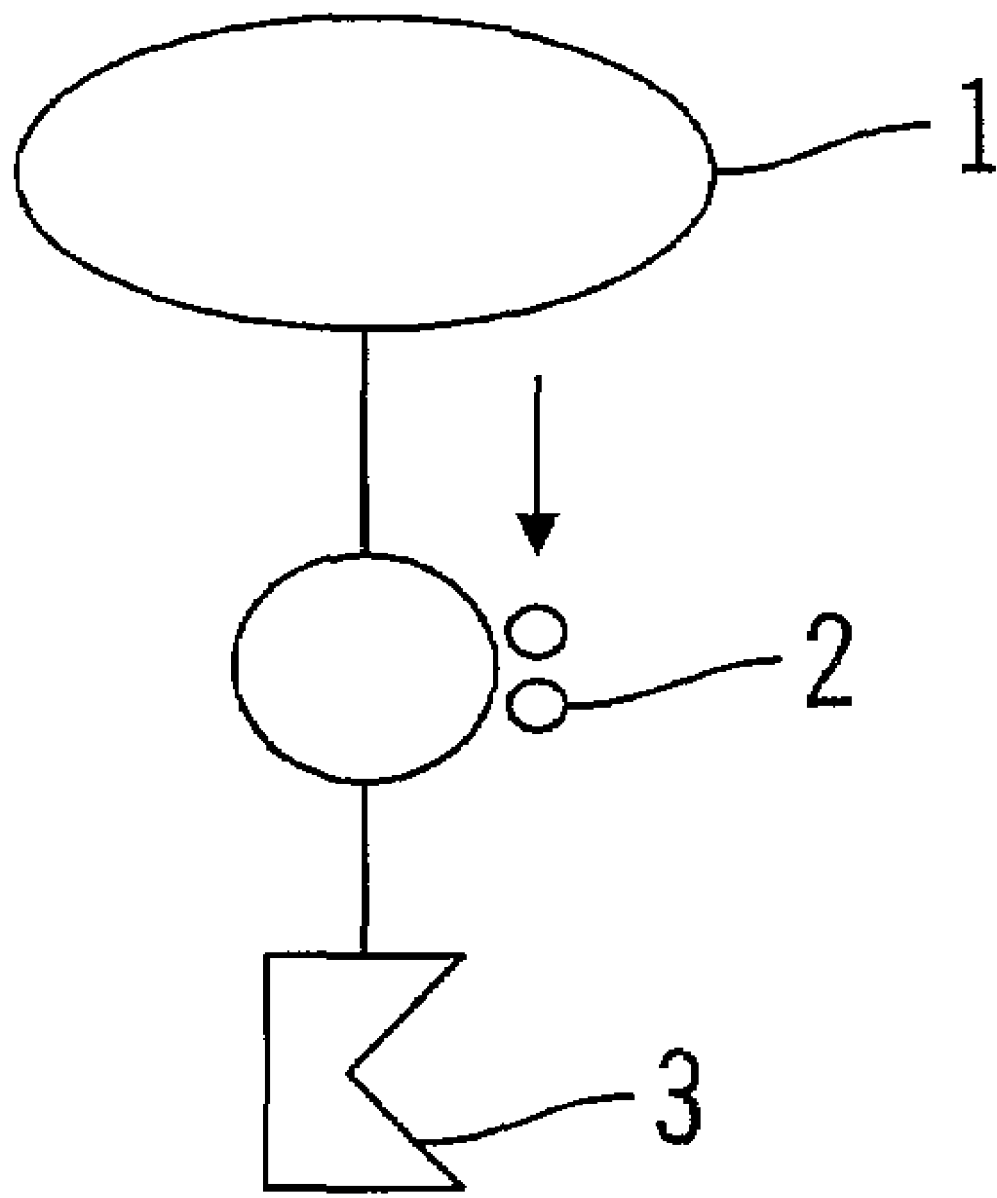
FIG. 2 shows a schematic of an acridine-based boronate biosensor molecule for use in embodiments of the invention that illustrates its three submolecular components.

As illustrated in FIG. 2, generalized biosensor molecules in accordance with embodiments of the invention include three submolecular components: (1) an acridine-based fluorophore, (2) a linker moiety, which typically includes an amine, and (3) a boronate substrate recognition/binding moiety, which binds to polyhydroxylate analytes, such as glucose. These biosensor molecules further include a "switch" element that is drawn from electronic interactions that involve these submolecular components.

This switch element is an integral component of the polyhydroxylate analyte sensing mechanism, i.e., transduction ability, of the biosensor molecules in accordance with embodiments of the present invention that serves to effectively "switch off" the fluorescence of the acridine-based fluorophore in the absence of bound polyhydroxylate analyte by donating electrons to the excited state of the fluorophore in an intramolecular photo-induced electron transfer (PET) process. Thus, in the absence of polyhydroxylate analyte binding, e.g., glucose binding, the acridine-based boronate biosensor molecules in accordance with embodiments of the invention exhibit excited states of the fluorphore that are essentially quenched by the switch element. On the other hand, in the presence of a polyhydroxyate analyte fluorescence is greatly enhanced from the low level background levels that can be observed in the absence of analyte. Consequently, the binding of a polyhydroxylate analyte, such as glucose, can be correlated with the ambient analyte concentrations via a change in fluorescence intensity and/or a change in fluorescence lifetimes of embodiments of the acridine-based boronate biosensor molecules of the invention.

Figure 5:
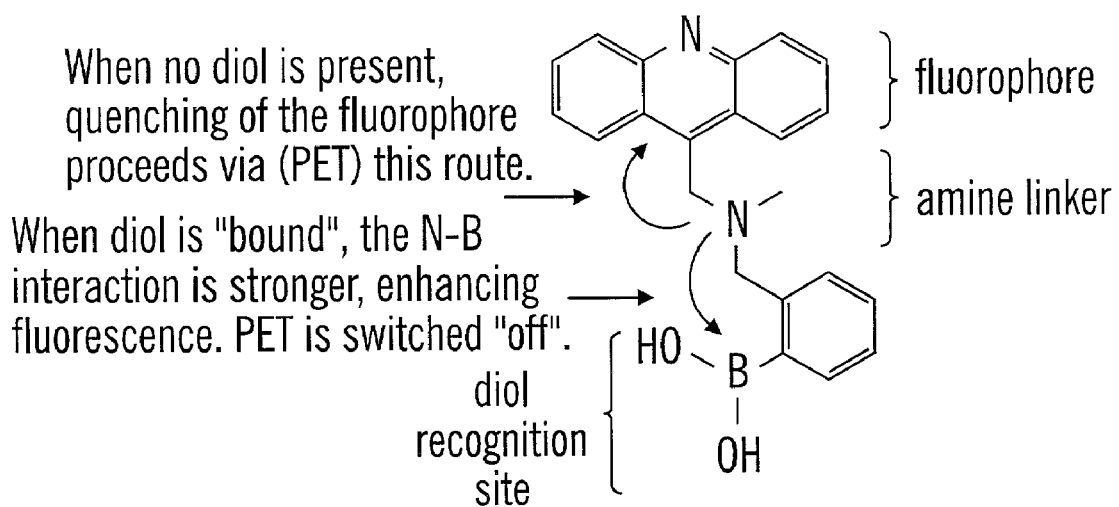
FIG. 5 is a schematic of the intramolecular photo-induced electron transfer (PET) mechanism that provides a "switch" element that electronically turns the fluorescence of the acridine-based boronate biosensor molecules in accordance with embodiments of the invention "on" and "off".

Without being limited by a particular theory or mechanistic scheme, the phenomenon of enhanced fluorescence in the presence of a polyhydroxylate analyte is schematically illustrated in FIG. 5 to aid an understanding of the behavior of the acridine-based biosensor molecules in accordance with embodiments of the invention. When glucose, for example, is bound to a phenylboronic acid of the substrate recognition moiety of an acridine-based boronate biosensor molecule, one way to explain the observed increase in fluorescence intensity is that a dative bond is produced between the electron-deficient boron atom of a substrate recognition moiety and a electron-rich atom of the linker moiety, generally an electron-rich nitrogen atom of an amine. Presumably, this boron-nitrogen "interaction" is a consequence of the complexation of an oxygen-rich analyte with the phenylboronic acid which leaves the boron atom of the substrate recognition moiety even more electron deficient. In this mechanistic scheme, the binding of the poly-hydroxylate analyte provides the electronic impetus for the unshared electrons of the electron-rich atom to be utilized in bonding to the electron-deficient boron atom, and thus, precludes these electrons from being available for transfer to the excited state of the acridine-based fluorophore. As a consequence, in the presence of a bound analyte, the fluorescence-quenching PET process is suppressed and the acridine-based fluorophore can essentially exhibit enhanced fluorescent properties, including emission intensities and lifetimes of its excited states. Moreover, this exhibited change in the fluorescent properties of the acridine-based boronate biosensor molecules in accordance with embodiments of the invention can be accurately correlated to the ambient glucose concentration, which in effect serves to "switch" the intrinsic fluorescence of the fluorphore "back on."

Thus, for embodiments of the acridine-based boronate biosensor molecules of the invention, the fluorescent switch element generally includes the boron atom of the substrate recognition moiety and the heteroatom of the linker moiety, preferably a nitrogen atom, but also includes the fluorophore in its electron-accepting capacity. As described above, this fluorescent switch is generally "off" in the absence of bound polyhydroxylate analyte and is generally "on" in the presence of bound polyhydroxylate analyte. Thus, the reversible binding of a polyhydroxylate analyte essentially turns the fluorescent switch "on" and "off". Although in the case of particular acridine-based biosensor molecules, this switching function is not an "all or none" phenomenon, as a certain level of background fluorescence is observed in the absence of polyhydroxylate analyte.

As shown in FIG. 2, the generalized acridine-based boronate biosensor molecule in accordance with embodiments of the invention includes an acridine-based fluorophore denoted as F. In embodiments of the biosensor molecules of the invention, this acridine-based fluorophore is the core fluorophore upon which substituents can be added to achieve desired electronic and/or chemical properties of a particular biosensor molecule. For example, substituents can be added that effect the absorption and emission wavelengths, the quantum yield and/or the fluorescence lifetimes of particular embodiments of the acridine-based boronate biosensor molecules. Additionally, substituents may be added that affect the solubility of the biosensor molecule and/or provide functionality that can be coupled to other molecules, such as a polymer matrix.

FIGS. 3(a–d) show some examples of preferred embodiments of the acridine-based boronate biosensor molecules. In these examples, substituents add desired functionality to the core acridine fluorphore. For embodiments of the acridine-based boronate biosensors of the invention, however, any chemical functionality added to the flurophore, or other moieties, is appropriate as long as the added substituents do not adversely affect the PET properties, i.e., switching function, of the resultant biosensor molecule in response to analyte binding, particularly in response to glucose binding. Moreover, the added substituent should not adversely affect the long wavelength emission properties of the resultant biosensor molecules. It is preferred that embodiments of the acridine-based boronate biosensor molecules of the invention emit light at about 450 nm or greater, even if these wavelengths are not the maximum wavelength of emission for the molecule.

An exemplary embodiment of an acridine-based boronate biosensor molecule of the present invention includes the Acridine Orange fluorophore (3,6-bis(dimethylamino)acridine), which is shown in FIG. 3(d). The specific substituents added to the acridine fluorophore to create acridine orange are two amino groups at positions 3 and 6 of the acridine core. These substituents increase both the absorption and emission wavelengths, as well as providing functionality that can be coupled to other molecules. This core Acridine Orange fluorophore can be further substituted either at these amino groups, preferably with lower aliphatic functional groups, or at other positions on the fluorophore. As with other embodiments of the acridine-based boronate biosensor molecules in accordance with embodiments of the invention, any chemical functionality is appropriate, as long as the substituents do not adversely affect the PET properties, or switching function, of the resultant biosensor molecule in response to analyte binding, particularly in response to glucose binding.

The substrate recognition moiety of embodiments of the acridine-based boronate biosensor molecules is preferably provided by a phenylboronic acid moiety, namely, $(C_6H_5)B(OR^1)_2$, where $R^1$ is hydrogen, a lower aliphatic or aromatic functional group. Preferably, $R^1$ is hydrogen. However, other substituted boronic acids also may be used in embodiments of the biosensor molecules provided that upon polyhydroxylate binding the electronic effects at the boron atom are not adversely affected so as to alter the PET properties of the resultant biosensor molecule, as noted above.

Further, the preferred embodiments of the acridine-based boronate biosensor molecules include a phenylboronic acid that is covalently bonded to an optional linkage, $L^1$, which is part of the linker moiety. This configuration is illustrated schematically in FIG. 1. Besides the $L^1$ linkage, the linker moiety also includes a heteroatom, labeled as Z, preferaby a nitrogen, however, the linker moiety may include a different electron-donating atom, such as oxygen, sulfur or phosphorous. The linker moiety further includes a second optional linkage, $L^2$, which provides a linkage to the acridine-based fluorophore. The linkages $L^1$ and $L^2$ are each generally 0–4 contiguous atoms selected from carbon, oxygen, nitrogen, sulfur, and phosphorous, and preferably are simple alkyl chains where n=0, 1, 2, 3, 4, 5, 6, 7, 8, or the like. Additionally, preferred linkers may contain polyethylene oxide (PEO), hydroxy alkyl and amino alkyl groups. Optional groups $R^2$, $R^3$ and $R^4$ are attached respectively to the phenyl group, the heteroatom of the linker moiety, and the fluorophore. These optional groups may be functional groups that achieved desired electronic effects or that can form covalent linkages to a polymer matrix, or the like. Alternatively, $R^2$, $R^3$ and $R^4$ may be hydrogen, an aliphatic, aromatic, acidic, $-NH_2$, $-OH$, SH, or NCO functional group.

Other embodiments of the acridine-based boronate biosensor molecules of the invention include a ditopic molecular design which is capable of binding one or more polyhydroxylate analytes, such as glucose. The range of sensitivity of monotopic acridine-based boronate biosensor molecules is approximately 80 mg/ml to about 1000 mg/ml. In these acridine-based boronate ditopic biosensor molecular designs, however, the signal to noise ratio of transduction in sub-100 mg/ml is improved due to the presence of two proximal boronate moieties which form a ditopic receptor. These ditopic biosensors may allow for cooperativity between the boronate binding groups and thus increase the affinity for polyhydroxylate analytes, such as glucose.

Figure 4:
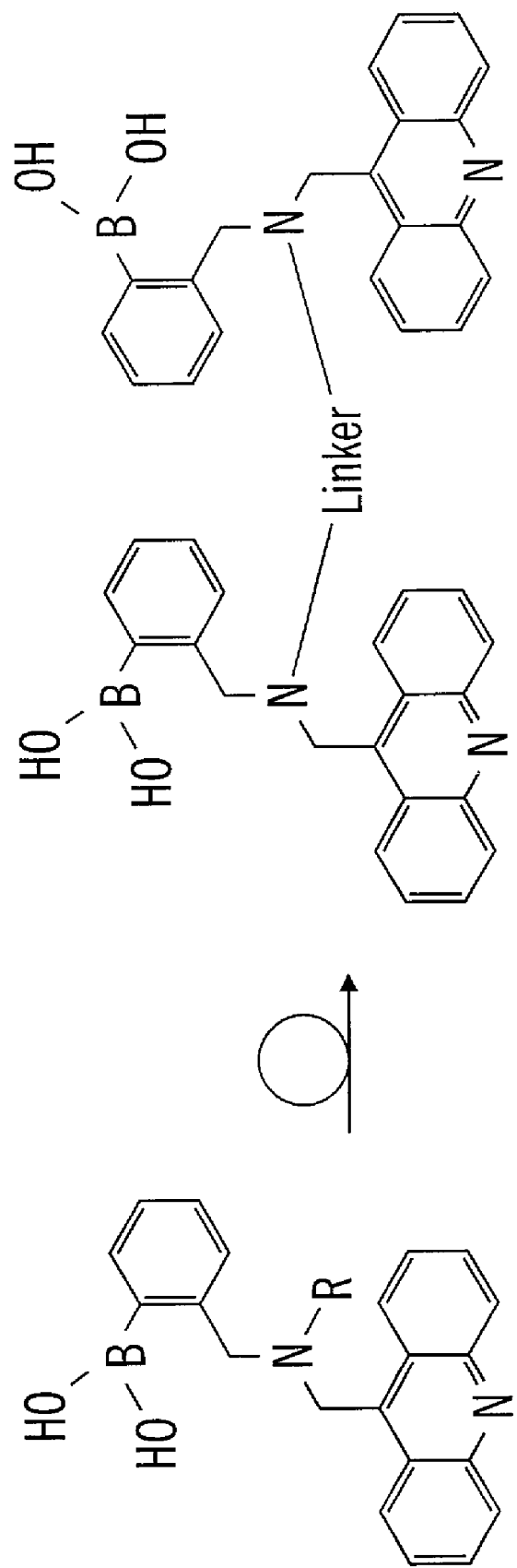
FIG. 4 illustrates a generalized scheme for the production of ditopic acridine-based boronate biosensor molecules in accordance with embodiments of the invention.
Figure 6:
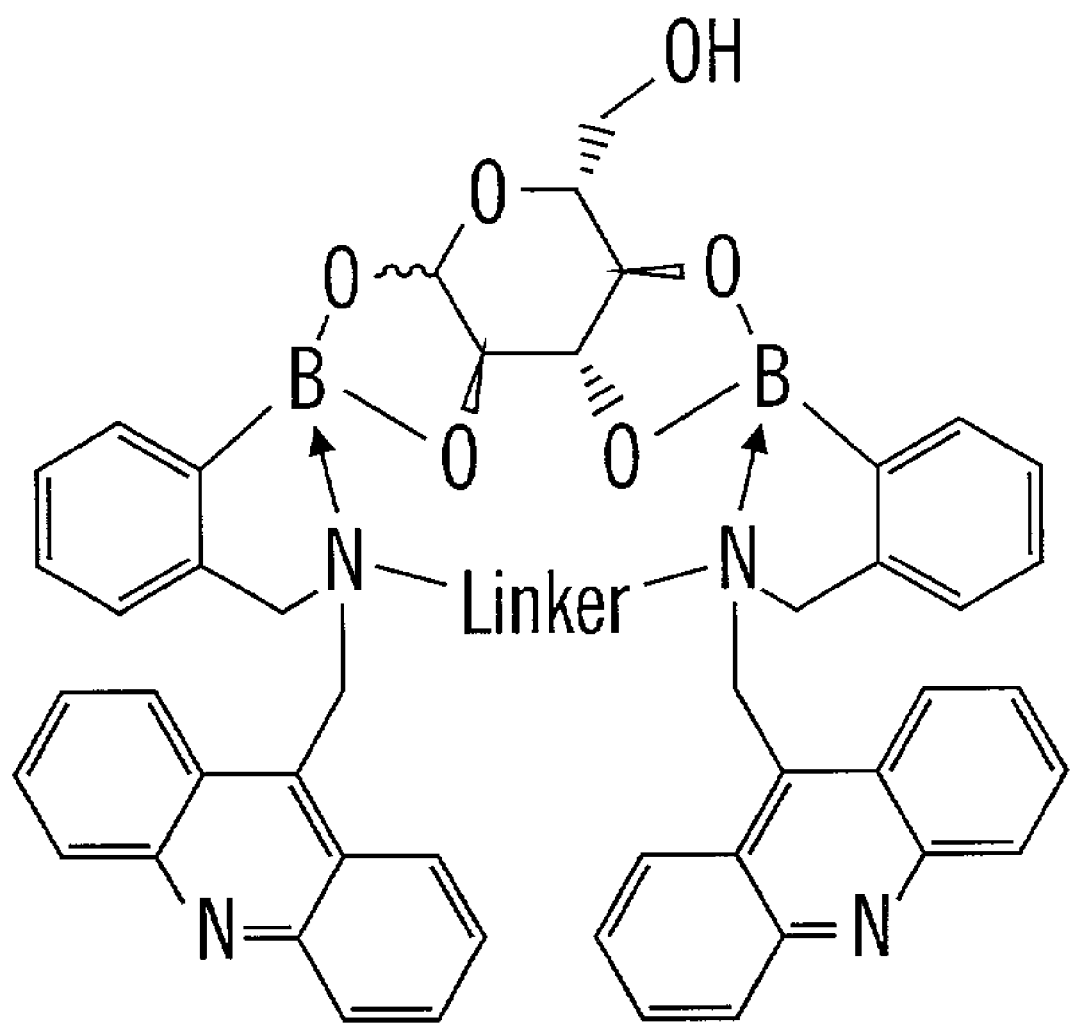
FIG. 6 illustrates a possible binding motif for a generalized ditopic acridine-based boronate biosensor molecule in accordance with embodiments of the invention.

The overall molecular design of a generic ditopic acridine-based boronate biosensor molecule is illustrated in FIG. 4. A possible binding motif for embodiments of the ditopic biosensors of the invention is illustrated in FIG. 6. As shown in this figure, a ditopic biosensor molecule is depicted as binding to one glucose molecule, which is the likely mode of binding at low glucose concentrations. At higher glucose concentrations, however, other binding modes are possible. In particular, at higher glucose concentrations, each boronate binding site of a ditopic acridine-based boronate biosensor molecule may bind a glucose molecule, yielding two bound glucose molecules for each ditopic biosensor molecule. Thus, the ditopic molecular design provides acridine-based boronate biosensor molecules with increased sensitivity for detecting polyhydroxylate analyte, especially at low concentrations of analyte.

Preferred embodiments of ditopic acridine-based boronate biosensor molecules of the present invention generally include two fluorophores and two boronate substrate recognition moieties. In these biosensor molecules, the two fluorophores and two binding sites may be the same or different. Other embodiments of the ditopic biosensor molecules of the invention, however, also include species where there is one fluorophore and two boronate substrate recognition/binding sites. This generalized molecular design is also capable of binding one or more polyhydroxylate analyte molecules, such as glucose.

The above description of the acridine-based boronate biosensor molecules of the invention illustrate the modular nature of these biosensor molecules. This modular architecture provides building blocks for future design of other biosensor molecules. Moreover, as shown in the examples below, these acridine-based boronate biosensor molecules provide a reliable model for fluorescent biosensor molecule development, which represents an advantage toward creating polyhydroxylate reporter molecules that have at least one desired fluorescent property, for example, but not limited to, operating at longer wavelengths. The model, therefore, allows for systematic build-up (i.e., component by component) of new acridine-based boronate biosensor molecules in relatively simple steps.

To use embodiments of the acridine-based biosensor molecules of the present invention for polyhydroxylate analyte sensing in-vivo, these biosensor molecules are generally immobilized in a polymer matrix to form implantable biosensors that can be placed under the skin. It is preferable, therefore, that the implanted biosensor molecule be incorporated/immobilized into a polymer matrix to prevent the acridine-based boronate biosensor molecules from diffusing into bodily fluids and being carried into the body.

Immobilzation of the biosensor molecules can involve entrapment by, encasement in, attachment to or the like, one or more polymer matrix materials. Further, attachment to a polymer matrix can involve covalent attachment or ionic attachment, such as a salt bridge. For in-vivo glucose sensing, embodiments of the acridine-based boronate biosensor molecules can be immobilized in a glucose permeable matrix to form an implantable acridine-based boronate biosensor than can be implanted cutaneously, subcutaneously, dermally, subdermally, or the like. For these implanted embodiments, the acridine-based biosensor may be in the form of a small patch, a bead, a disc, or the like, which is implanted beneath the skin. These implants may be implanted subcutaneously or may be part of a transcutaneous implant, such as the embodiment illustrated in FIG. 8, where the implanted acridine-based biosensor is placed at one end of a wire with an optical fiber. In either case, embodiments of the biosensor of the invention generally can be implanted about a few millimeters beneath the skin. Complete subcutaneous implants are generally placed about 1–2 mm beneath the skin. Fiber optic or transcutaneous implants, on the other hand are generally placed about 1–4 mm beneath the skin. Other embodiments may be implanted with the detection hardware and a transmitter (not shown). These embodiments may be implanted anywhere in the body where there is sufficient space and sufficient bodily fluids to obtain a measure of analyte concentration levels.

The polymer matrix used for immobilization can either be prepared from biocompatible materials or coated with biocompatible materials. Moreover, the polymer matrix may include a mixture of polymers or copolymers that maintain certain desired conditions of the internal biosensor milieu, such as pH and solubility of implantable biosensors and biosensor molecules. Preferably, at least the outer surfaces of the implantable biosensor should include, or be coated with, at least one biocompatible material, as these surfaces are to be in contact with human tissue and body fluids. As used herein, the term "biocompatible" refers to a property of a material or matrix that produce no substantial adverse effects upon implantation in the body. The biocompatible polymer matrix also must be permeable to the analyte of interest. For example, in the case of sensing glucose in-vivo, the biocompatible polymer matrix should be permeable to glucose and be stable within the body for the lifetime of the implant.

Figure 7:
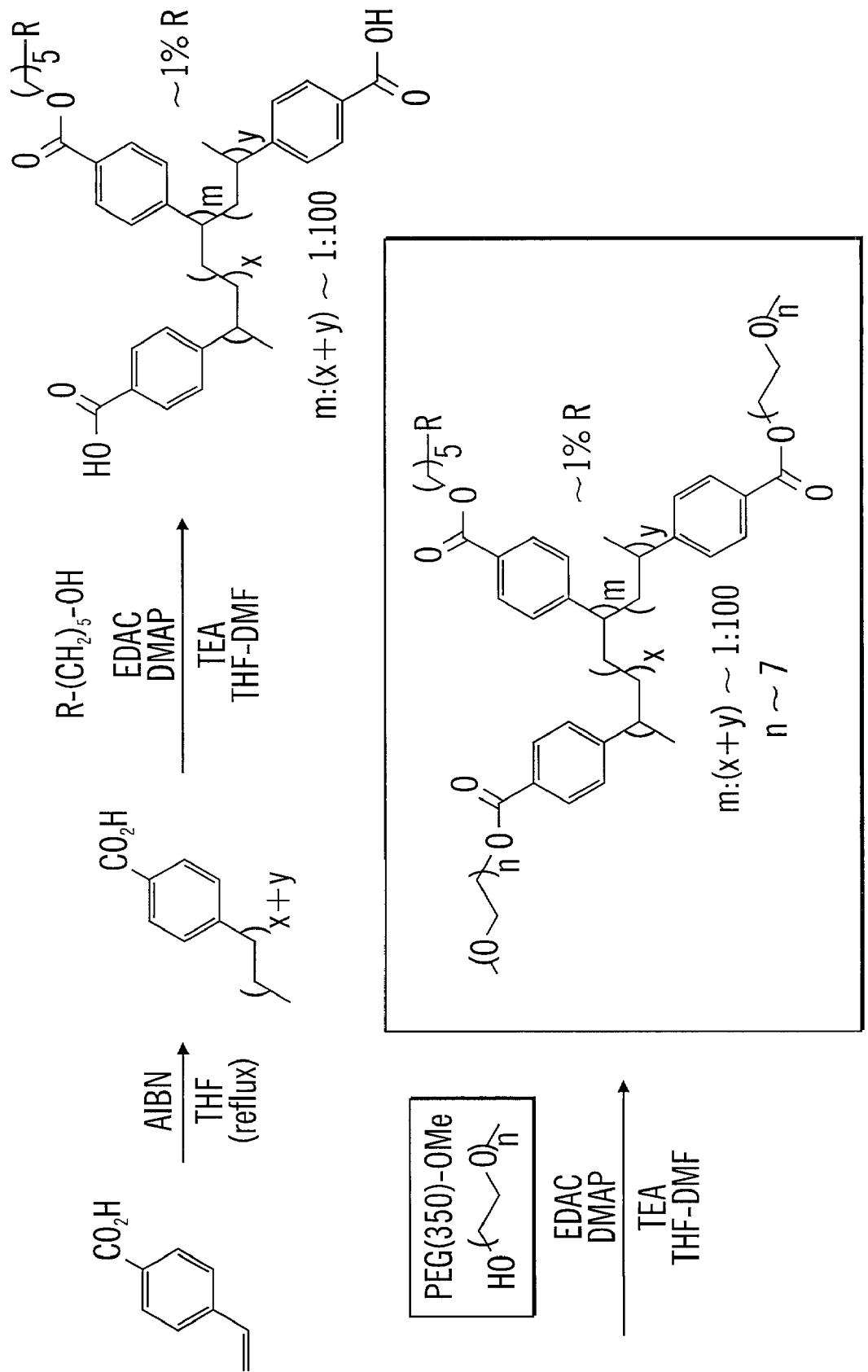
FIG. 7 depicts a reaction scheme for incorporating an acridine-based boronate biosensor molecule into a polycarboxystyrene polymer matrix, where R represents any acridine-based boronate biosensor molecule.

Further, the polymer matrix can include either a liquid substrate (e.g., a dialysis tube that contains acridine-based biosensor molecules in accordance with embodiments of the invention attached to a water-soluble polymer matrix) or a solid substrate (e.g., acridine-based biosensor molecules in accordance with embodiments of the invention attached to a water-insolube polymer-matrix, such as polyurethanes, polystyrenes, polyacrylates, polyureas, silicon-containing polymers, pHEMA, hydrogels, solgels, copolymers thereof, mixtures thereof or the like. FIG. 7 depicts a reaction scheme for incorporating an acridine-based boronate biosensor molecule into a polycarboxystyrene polymer matrix, where R represents any acridine-based boronate biosensor molecule. Additionally the polymer matrix can include a biocompatible shell prepared from, for example, dialysis fibers, telfon cloth, resorbable polymers or islet encapsulation materials. Further, the polymer matrix that encompasses the acridine-based boronate biosensor molecules can be in any compact form, such as a small disc, cylinder, patch, micorsphere, refillable sack, or the like, and can further incorporate a biocompatible mesh that allows for full tissue regrowth and vascularization.

Particular embodiments of the implantable acridine-based biosensor may include water-soluble polymers that are functionalized with the fluorescent biosensor molecules, such polymers include polyethylene glycol (amino-terminated), Jeffamine polymers (2-propyl amino terminated block-polypropylene oxide block-polyethylene oxide block-polypropylene oxide), poly(vinyl alcohol), poly(acrylic acid), linear pHEMA copolymers thereof or the like. Because these polymers are water-soluble, they must be placed inside a microporous container, shell or the like that is permeable to glucose, is suitable for implantation, i.e., the container, shell or the like must be biocompatible. Examples of such microporous polymeric materials are linear polyesters of carbonic acid, poly(vinylchloride), polyamides, polychloroethers, polyurethanes, polyimides, copolymers thereof, mixtures thereof or the like. Examples of some of these polymers functionalized with acridine-based boronate biosensor molecules are shown in FIG. 15. These water-soluble polymers possess some distinct advantages over other types of fluorescent biosensor molecule-functionalized polymers. These advantages include favorable solution behavior for improved polyhydroxylate analyte recognition and binding, i.e., improved kinetics, as well as reasonably straightforward chemistry for attachment of acridine-based boronate biosensor molecules.

Other implant embodiments of the acridine-based biosensors of the invention can be formulated similar to a reusable implant embodiments described in WO 01/01851, published on Jan. 11, 2001, which includes a reusable analyte sensor site for use with the acridine based biosensor in accordance with embodiments of the invention. WO 01/01851 is incorporated by reference and is attached as Appendix A. If a sealable port is included in embodiments of the implantable biosensors of the invention, the port may be useful for refilling the implant with fresh biosensor molecules, or biosensor molecules attached to a polymer matrix, without removing the implant.

Figure 16:
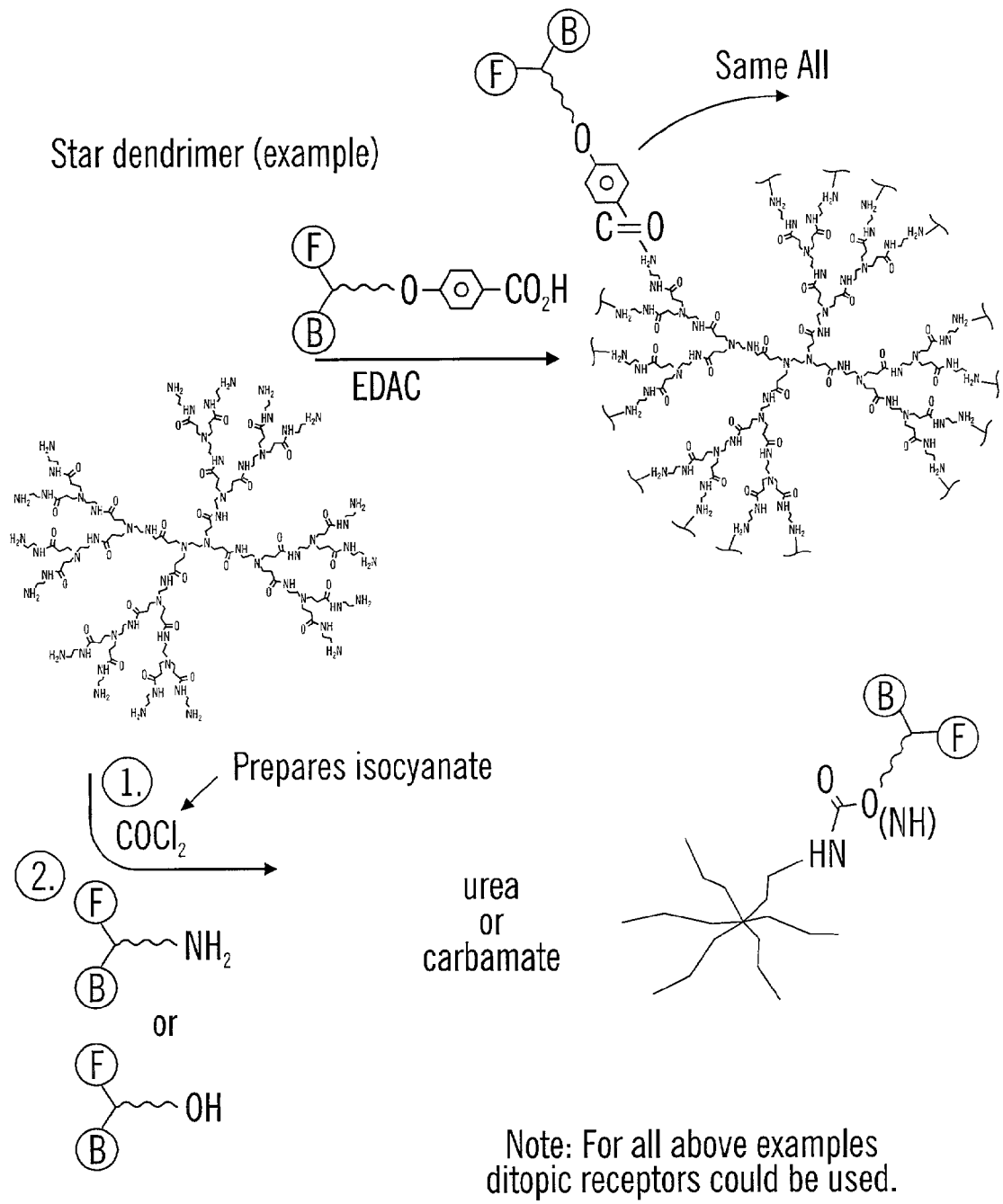
FIG. 16 depicts some preferred embodiments of acridine-based biosensor molecules attached to multiple attachment-point polymers.

Also included in particular embodiments of the invention are acridine-based boronate biosensor molecules attached to polymers with multiple attachment points, such as a relatively new class of polymers called star dendrimers. Several examples of multiple-attachment point, star dendrimers polymers functionalized with an acridine-based boronate biosensor molecule in accordance with embodiments of the invention are shown in FIG. 16. Polymers with multiple attachment points for functionalization with fluorescent biosensor molecules in accordance with embodiments of the invention possess some favorable properties. First, these polymers do not require encapsulation for them to be effective in analyte sensing. Further, some of these polymers possess appropriate characteristics for use as a biomaterial, i.e, mechanical strength, hydrophilicity, purity, and the like. Examples of the materials suitable for use with multiple-attachment point polymers are cross-linked poly(vinyl alcohol), cross-linked poly(acrylic acid), star dendrimers, copolymers thereof, mixtures thereof or the like.

The implantable acridine-based boronate biosensors in accordance with embodiments of the invention are suitable for long term use beneath the skin. Long term use can be about one month or less to about a year. For long-term implants, embodiments of the implantable, acridine-based boronate biosensor may further include one or more adhesion coatings, which preferably are biologically active materials that facilitate attachment of cells to the biocompatible matrix, such as extracellular matrix molecules (ECMs) including laminins, tenascins, collagens, netrins, semaphorings, thrombosphodins, fibronectins, vitronectins, proteoglycans, biologically active fragments thereof, mixtures thereof, or the like. These adhesion coatings are advantageous in facilitating diffusion limited reactions by shortening the diffusion distance from the host to the interior of the implants. Additionally, these adhesion coatings may include cell—cell adhesion molecules (CAMS), such as the caherin superfamily, fibernectins, selectins, integrins, biologically active fragments thereof, mixtures thereof or the like, or immumoglobin (Ig) superfamily molecules, such as intercellular cell adhesion molecule (ICAM), or the like. Long-term embodiments of the implantable, acridine-based boronate biosensor may also include an angiogenic coating, which aids in the development of new capillary blood vessels in a tissue resulting in improvement in oxygen and nutrient supply at the implantation site. Examples of angiogenic factors include vascular endothelial growth factor (VEGF), acidic fibroblast growth factor (AFGF), basic fibroblast growth factor (BFGF), transforming growth factor-beta, platelet-derived endothelial cell growth factor, angiogenin, tumor necrosis factor-alpha, bone morphogenic protein (BMP), biologically active fragments thereof, mixtures thereof, or the like.

Embodiments of a biosensor system that include acridine-based boronate biosensor molecules also are provided for in the present invention. These biosensor systems further include an optical system for interrogating the acridine-based boronate biosensor molecules in-vivo. As used herein, the term "interrogating" refers to illumination of the acridine-based boronate biosensor molecules contained within an implantable polymer matrix and subsequent detection of emitted light. A schematic which generally represents a transdermal optical system, in accordance with embodiments of the invention, is shown in FIG. 9, where the light source (S) shines light through the skin and a detector (D) detects the fluorescence transmitted through the skin.

Figure 8:
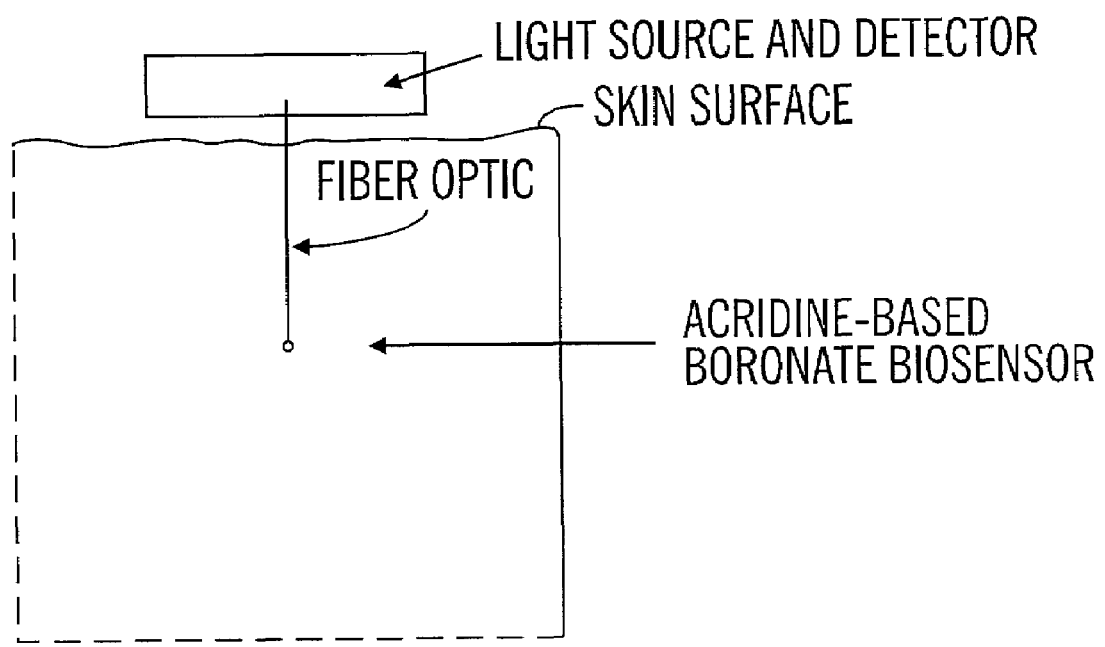
FIG. 8 shows a transcutaneous acridine-based boronate biosensor system in accordance with embodiments of the invention.

Because of the long wavelength operating range of the acridine-based boronate biosensors in accordance with embodiments of the invention, these biosensors can be interrogated by applying excitation light through the skin and externally monitoring the intensity, or lifetime, of the emitted fluorescence, for example. The measurement of the emitted light thus allows the in-vivo concentration of a polyhydroxylate analyte, such as glucose, to be quantified. Other embodiments include acridine-based biosensors optical systems where there is no direct transmission through the skin, as the light source is also implanted or light travels to subcutaneous space via a fiber optic to the acridine-based boronate biosensor molecules encompassed within the implanted biosensor. This later fiber optic embodiment is depicted in FIG. 8. Still other embodiments of the biosensor systems include configurations where both the light source and detector are implanted.

Figure 9:
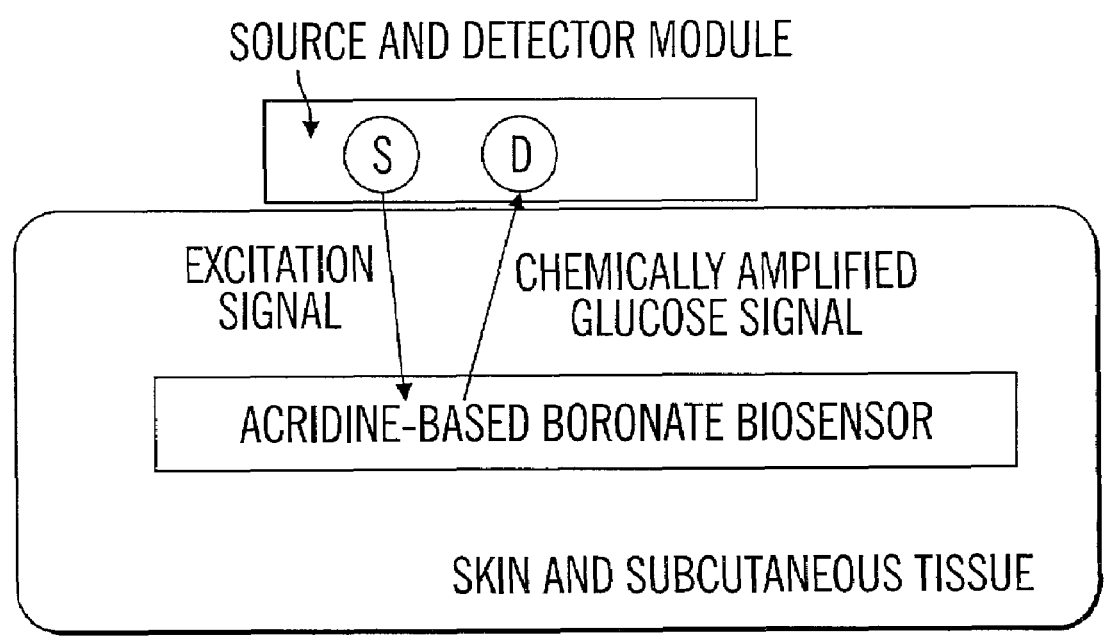
FIG. 9 is a generalized schematic representation of the acridine-based boronate biosensor systems in accordance with embodiments of the invention.

FIG. 9 shows a generalized schematic of a subdermally implanted optical biosensor system in accordance with embodiments of the present invention. The light source could be a lamp, an LED, a laser diode (pulsed or modulated), or the like. The detector could be a photodiode, a CCD detector, photomultiplier tube, or the like. Optionally, filters are used to filter the incident and/or emitted beams of light to obtain the desired wavelength. The source and detector are shown in FIG. 9 as positioned outside the body, although the source and/or detector can be implanted within the body. The acridine-based boronate biosensor molecules in accordance with embodiments of the invention are contained within, or attached to, a polymer matrix to form a biosensor, and the biosensor is implanted beneath the skin. Preferably, the outer surfaces that are in contact with human tissue and body fluids are biocompatible. The light source is then used to illuminate the implanted biosensor and the detector detects the a signal which is usually emitted fluorescent light, or emitted fluorescent light that can be related to the fluorescence lifetimes of the acridine-based boronate biosensor molecules. Other forms of a signal also can be detected, such as absorbance, reflectance or transmittance, when a change in the amount of light or spectral character of light that is detected and measured is modulated by the local analyte concentration. In the case of fluorescence, a ratio of intensity of excitation and emission can be used to further verify the glucose signal. In preferred embodiments of the invention, the ratio of fluorescence from the acridine-based boronate biosensor molecules to the fluorescence of a calibration fluorophore can be measured to improve the accuracy of the measurement of analyte concentration. This method can eliminate errors of light transmission through the skin, for example.

EXAMPLES

Figure 10:
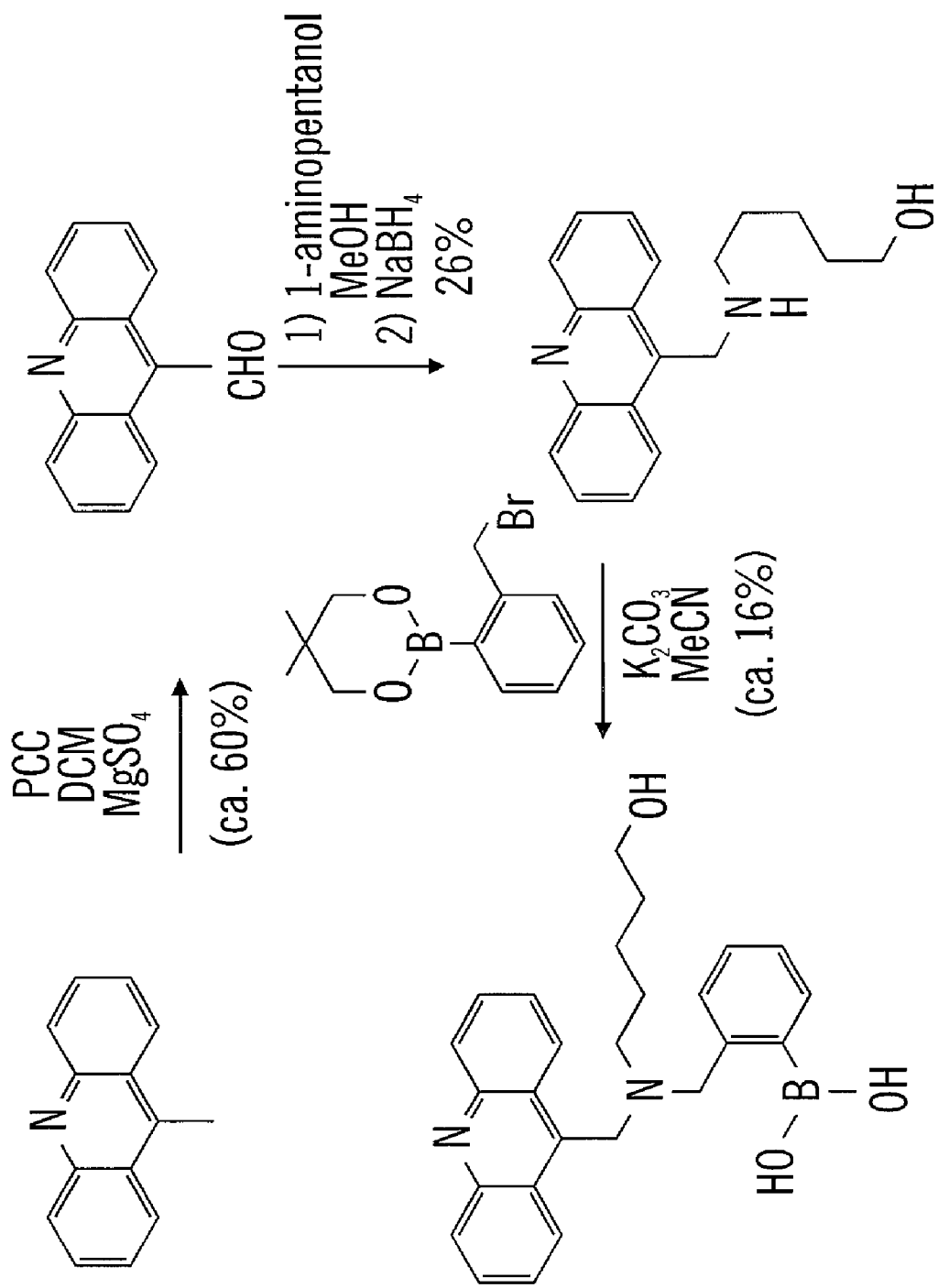
FIG. 10 shows a synthetic scheme for the production of a ACRAB acridine boronate biosensor molecule in accordance with embodiments of the invention.
Figure 11:
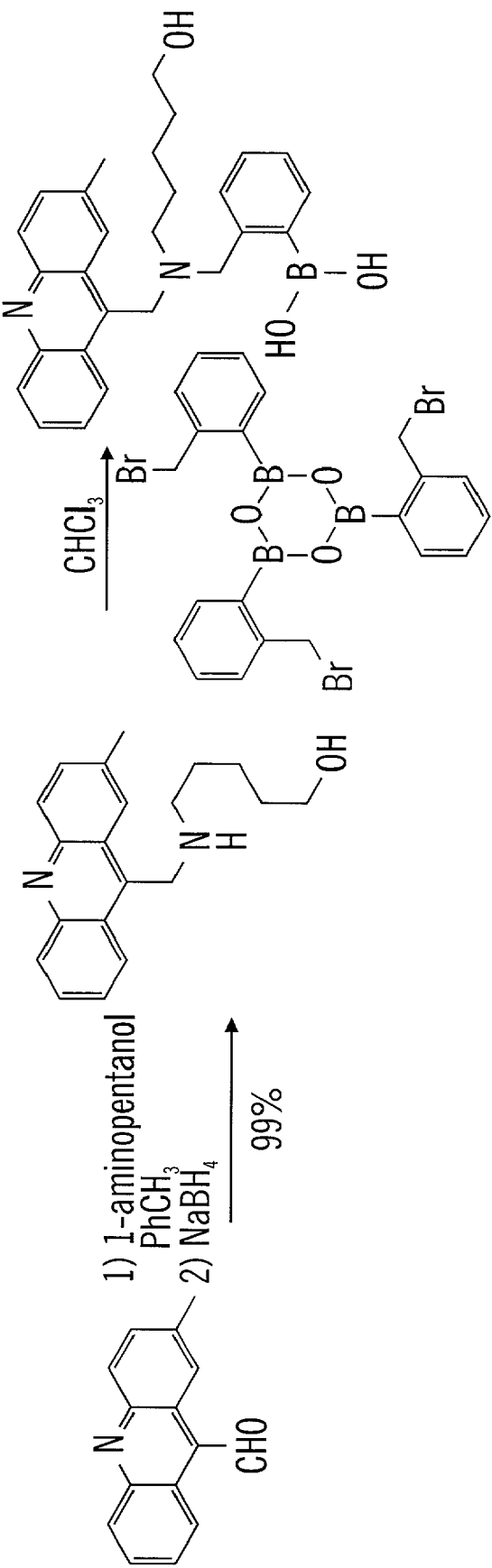
FIG. 11 shows a synthetic scheme for the production of a MEACRAB methylacridine boronate biosensor molecule in accordance with embodiments of the invention.
Figure 12:
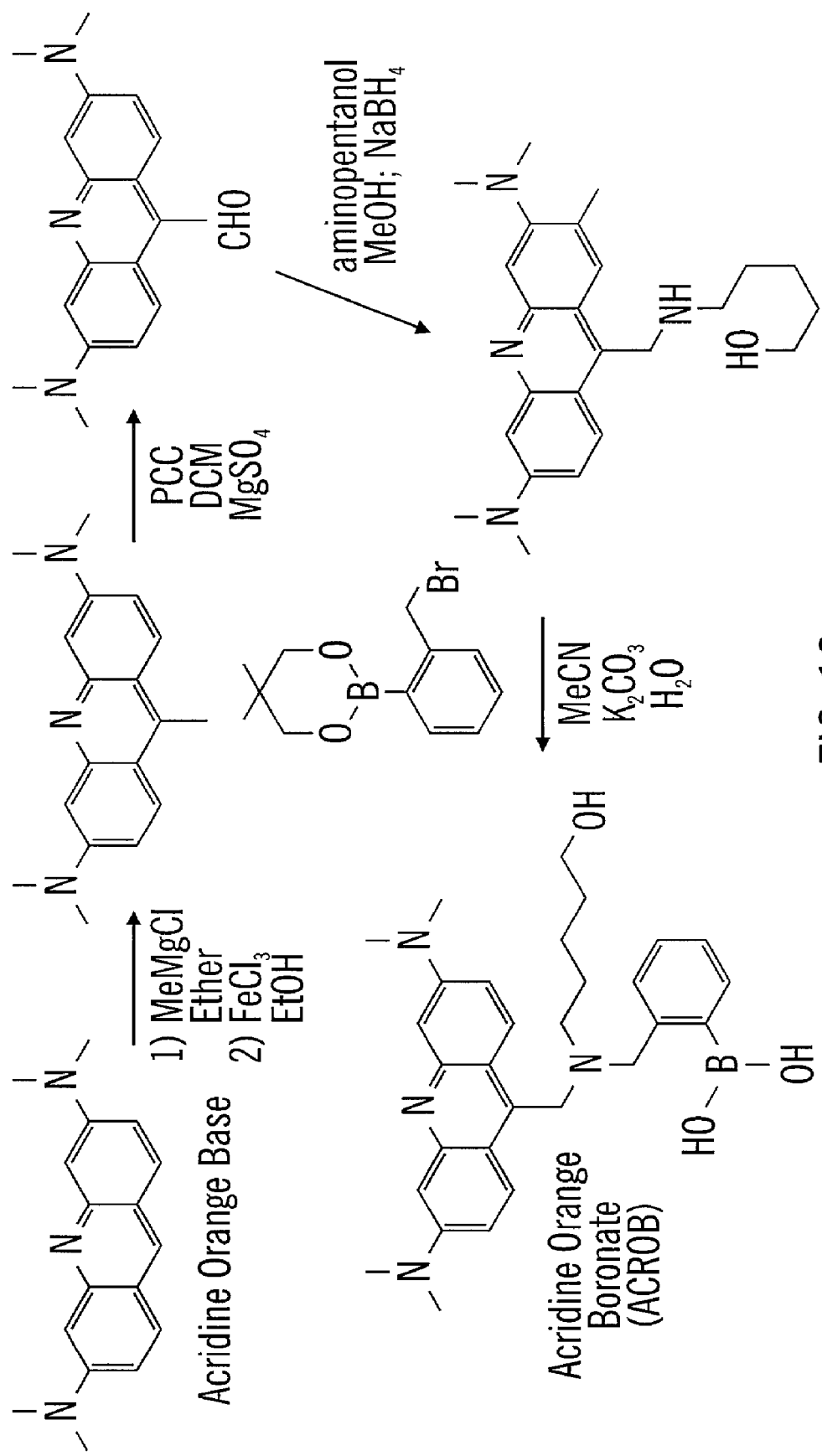
FIG. 12 shows a synthetic scheme for the production of the Arcridine Orange boronate biosensor molecule in accordance with embodiments of the invention.

1. Synthetic Methods of Making Embodiments of the Acridine-Based Boronate Biosensor Molecules of the Invention The following methods outlined the synthetic steps of making particular embodiments of the acridine-based boronate biosensor molecules of the invention. These particular embodiments are ACRAB (aminomethylhydroxypentyl-acridine boronate) and MEACRAB (aminomethylhydroxypentyl-methylacridine boronate), both of which are monotopic biosensor molecules, i.e., biosensor molecules including a singular polyhydroxylate recognition/binding site. The synthetic schemes for the production of ACRAB and MEACRAB are shown in FIG. 10 and FIG. 11, respectively.

i) Acridine-Based Boronate Biosensor Molecules a) Intermediate Biosensor Products Acridine-9-carboxaldehyde: 9-Methylacridine (500 mg., 2.59 mmol) was added to a 20 ml vial equipped with a stir bar. Dichloromethane (DCM)(15 ml) was added and the mixture was stirred vigorously until a clear yellow solution was obtained. Pyridnium chlorochromate (586 mg, 2.72 mmol) was added to the resultant yellow solution followed by MgSO$_4$ (1.5 mg). The resultant brown suspension was stirred at ambient temperature for 12 h. The mixture was filtered through a pad of silica and eluted with dichloromethane. The desired filtrate was collected, dried over Na$_2$SO$_4$ and concentrated under reduced pressure. The solid was dried under high vacuum to yield 846 mg of a yellow oil. $^1$H NMR analysis indicated that the sample was impure, containing 58% of the desired aldehyde. Three products were identified by $^1$H NMR: the desired aldehyde (acridine-9-carboxaldehyde 58%), a reduced alcohol (25%) and starting material (17%). A fourth product, presumably acridine-9-carboxylic acid is another by-product of the Canizzarro Reaction and remains trapped on the filter pad of silica.

Aminomethylhydroxypentylacridine (5[(acridin-a-ylmethyl)amino-pentan-1-ol): Approximately 90 mg of crude acridine-9-carbox-aldehyde was added to a 100 ml round-bottomed flask containing MeOH (8 ml) and a stir bar. 100 mg (1 mmol) aminopentanol was then added to the resultant solution. The solution was stirred at ambient temperature for 8 h. 44 mg (1.2 mmol) NaBH$_4$ was then added to the mixture and the solution stirred for an additional 9 h. This solution was poured into a solution of 1N HCl (20 ml) and washed with dichloromethane (3×40 ml). The aqueous layer was neutralized with 1N NaOH (40 ml) and extracted with dichloromethane (4×40 ml). The organic layer was dried over MgSO$_4$, filtered, concentrated under reduced pressure and finally dried under high vacuum to yield 98 mg of a yellow oil that solidifies upon standing. The product is light sensitive and should be kept refrigerated in the dark when not in use. The purity of the resultant material was checked by TLC (Silica 10:1 DCM:MeOH v/v) and $^1$H NMR. The $^1$H NMR analysis is given below.

$^1$H NMR (400 MHz, CDCl$_3$) δ: 8.32 (d; 2H; J=8 Hz), 8.23 (d; 2H; J=8 Hz), 7.77 (t; 2H; J=8, 1 Hz), 7.59 (t; 2H; J=8, 1 Hz), 4.72 (s; 2H), 3.61 (t; 2H; J=6 Hz), 2.85 (t; 2H; J=7 Hz), 1.54 (m; 4H), 1.42 (m; 4H) $^{13}$C NMR (100 MHz, CDCl$_3$) δ: 148.8, 130.4, 129.9, 129.1, 126.2, 125.2, 124.1, 62.7, 50.4, 45.0, 32.5, 29.7, 23.4.

Hydroxypentylaminomethylacridine (5((2-methyl-acridin-9-ylmethyl)amino)-pentan-ol): 2-methylacridine-9-carboxaldehyde (107 mg., 0.484 mmol) and toluene (35 ml) were added to a 25 ml round-bottomed flask equipped with a stir bar, condenser and a Dean-Stark apparatus. 5-aminopentan-1-ol (50 mg, 0.484 mmol) was added to the solution and the reaction mixture was heated under reflux for 6 h. Toluene was removed by distillation and the resultant oil was cooled to room temperature. Anhydrous MeOH (10 ml) was added and the solution was stirred under an atmosphere of nitrogen. NaBH$_4$ (20 mg, 0.53 mmole.) was added and the reaction stirred for 2 h. The solution was quenched with 1N HCl, stirred for 15 min, then neutralized with 1N NaOH. The solution was extracted with dichloromethane (2×50 ml), washed with brine (30 ml) and dried over Na$_2$SO$_4$ for 2 h. The suspension was filtered and the filtrate concentrated under reduced pressure followed by drying under high-vacuum. The yellow oil solidified upon standing and was stored in the refrigerator until further use. The final mass was 149 mg (99% yield). The $^1$H NMR analysis is given below.

$^1$H NMR (360 MHz, CDCl$_3$) δ: 8.29 (d; H; J=9 Hz), 8.22 (d; H; J=9 Hz), 8.13 (d; H; J=9 Hz), 8.04 (s; H), 7.74 (t; H; J=9), 7.60 (m; 2H), 4.69 (s; 2H), 3.63 (t; 2H; J=6 Hz), 2.86 (t; 2H; J=6 Hz), 2.58 (s; 3H), 1.54 (m; 4H), 1.42 (m; 4H).

b) Final Biosensor Molecules

ACRAB: Aminomethylhydroxypentyl-acridine (5[(acridin-9-ylmethyl)amino]-pentan-1-ol) (52 mg, 0.18 mmol) was added to a 25 ml, round-bottomed flask along with 2-bromomethylphenylboronic acid, neopentyl glycol ester (50 mg, 0.18 mmol) and 6 ml of MeCN. The solution was stirred under nitrogen to reflux. Potassium carbonate (122 mg, 0.88 mmol, 5 eq.) was added in one portion and the suspension heated under reflux for two hours. The reaction mixture was filtered, concentrated, purified by preparatory TLC and eluted with DCM/MeOH 20/1 v/v to yield 12 mg (16%) of a yellow solid, which is the aminomethylhydroxypentyl-acridine boronate or ACRAB). The $^1$H NMR sample contains a 1:1 impurity of neopentylglycol. The NMR shifts are consistent with a free species and not a protected boronate. Further evidence for a 1:1 adduct is given in the FABMS (Fast Atom Bombardment Mass Spectroscopy). The $^1$H NMR analysis is given below:

$^1$H NMR (400 MHz, CDCl$_3$) δ: 8.40 (d; 2H; J=9 Hz), 8.13 (d; 2H; J=9 Hz), 7.73 (t; 2H; J=9, 1 Hz), 7.50 (t; 2H; J=8, 1 Hz), 7.37 (dd; H), 7.32 (t; 2H), 7.23 (t; 2H), 4.41 (s; 2H), 3.94 (s; 2H), 3.56 (s; 4H), 3.34 (t; 2H; J=7 Hz), 2.42 (t; 2H; J=7 Hz), 1.54 (m; 2H), 1.18 (m; 2H); 1.06 (m; 2H).

MS(FAB, Cs): 497 (M$^+$+, 100).

Figure 17:
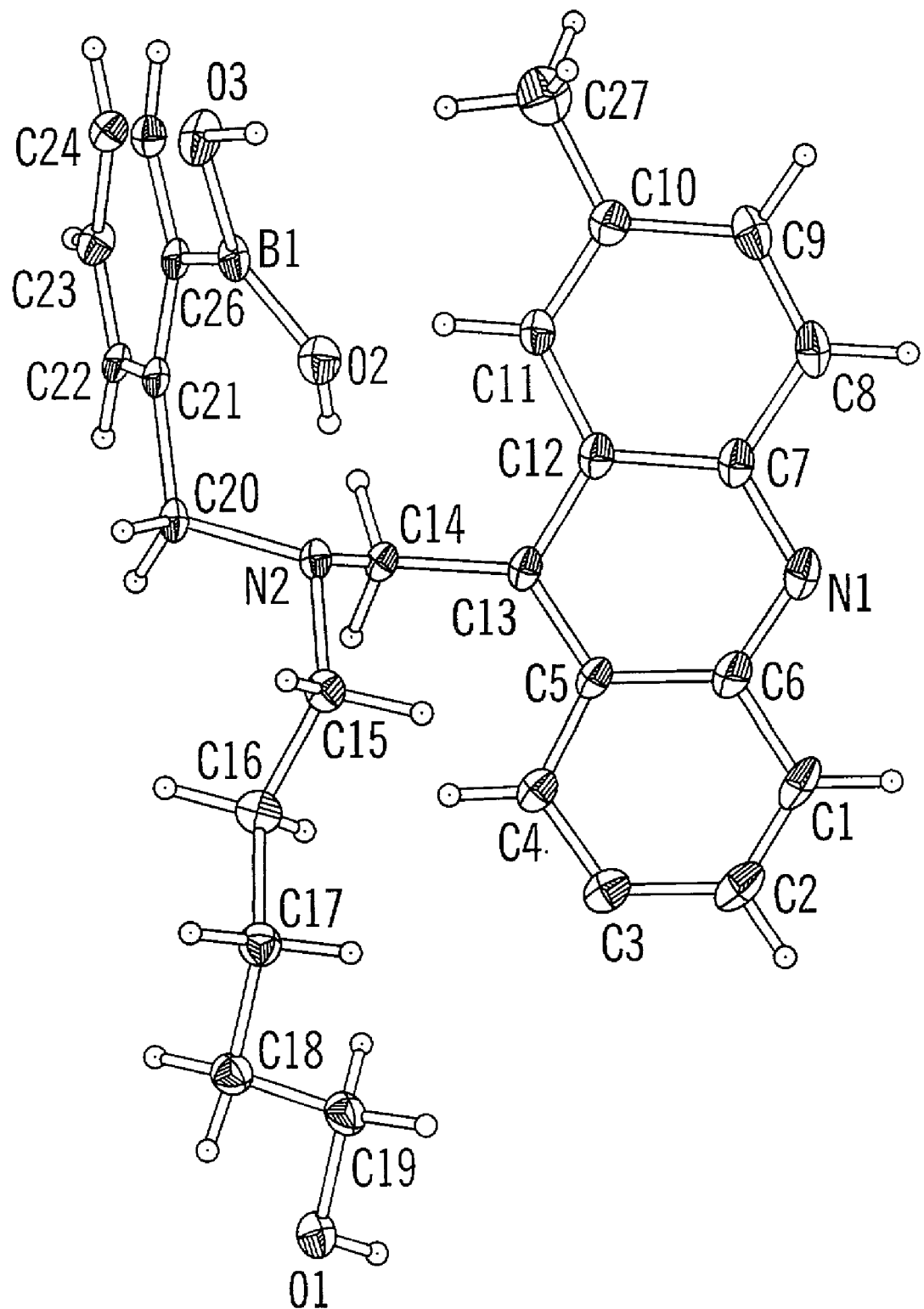
FIG. 17 shows the molecular structure of MEACRAB determined by x-ray crystallography.

MEACRAB: A 100 ml round-bottomed flask was equipped with a stir bar condenser and a nitrogen inlet adapter. The flask was charged with hydroxypentylaminomethylacridine (150 mg, 0,484 mmol) and 2-bromomethylphenylboronic acid (48 mg, 0.08 mmol) in 50 ml chloroform. 2-bromomethylphenylboronic acid had been converted to the boronic anhydride via azeotropic distillation in toluene prior to use. The mixture was heated at reflux for 2 h and cooled to ambient temperature. The sample was concentrated under reduced pressure and dried under high vacuum for 2 h. The solid was treated with MeCN/H$_2$O (4/1; v/v), the flask covered with aluminum foil and allowed to sit open to the air on the benchtop overnight. The resultant bright yellow crystals were collected by filtration and rinsed with MeCN/H$_2$O (4/1; v/v). The crystals were washed with water and the resultant material was dried under high vacuum for 2 h. A crystal was taken for determination of its structure by X-ray crystallography. The X-ray crystallography structure is shown in FIG. 17, and the crystallography data is given in Appendix B. The $^1$H NMR and FABMS data are given below:

$^1$H NMR (360 MHz, CDCl$_3$) δ: 8.33 (d; H; J=9 Hz), 8.11 (d; H; J=9 Hz), 8.02 (d; H; J=9 Hz), 7.97 (s (br); H), 7.80 (t; 2H; J=7 Hz), 7.67 (d; H; J=9 Hz), 7.59 (t; H; J=7 Hz), 7.40 (m; H), 7.32 (m; 2H), 5.59 (s; 2H), 4.65 (s (br); 2H), 3.99 (s; 2H), 3.55 (t; 2H; J=6 Hz), 2.58 (m; 2H), 2.56 (s; 3H; J=7 Hz), 1.60 (m; 2H), 1.29 (m; 2H); 1.06 (m; 2H).

MS(FAB Cs m/z (%): 443 (M$^+$H, 100); 850 (2MH$^+$–2H$_2$O, 25); 1274 (3M$^+$+2H$^+$–3 H$_2$O, 1).

Other Acridine-Based Boronate Biosensor Molecules: The fluorophores shown below are examples functionalized acridine-based fluorphores that are suitable for use in embodiments of the present invention. These fluorophores embodiments yield acridine-based boronate biosensor molecules with substantial emission at greater than 500 nm, thereby allowing for greater transmission through the skin and tissue. For light transmission through human dermal layers, substantial emission at about 550–600 nm is generally required. The structure in the upper left is a derivative of Acridine Orange. Acridine Orange has a maximum emission of 525 nm and its emission profile is detectable out to 575–600 nm. The tetranitroacridine derivative (upper right)

should also display similar emission wavelengths. Finally, other variants of acridine are proposed (bottom center) in which there are at least two substituents either one or both substituents are electron withdrawing (e.g., nitro) and/or electron donating (e.g., OMe) to push the fluorophore emission beyond 525 nm.

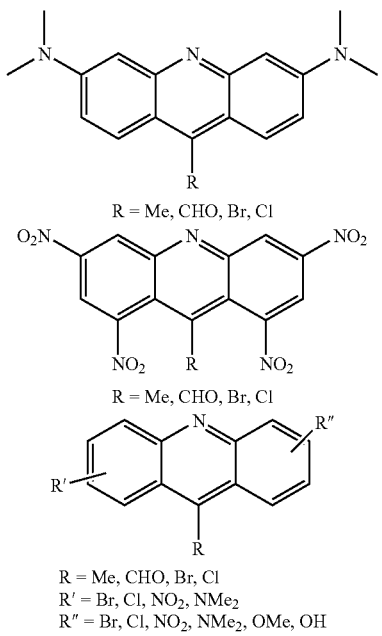

Post modification of these fluorophores is easily accomplished via similar synthetic routes as those outlined above for the ACRAB and MEACRAB embodiments of the acridine-based boronate biosenor molecules of the invention. These syntheses will generally be performed as follows:

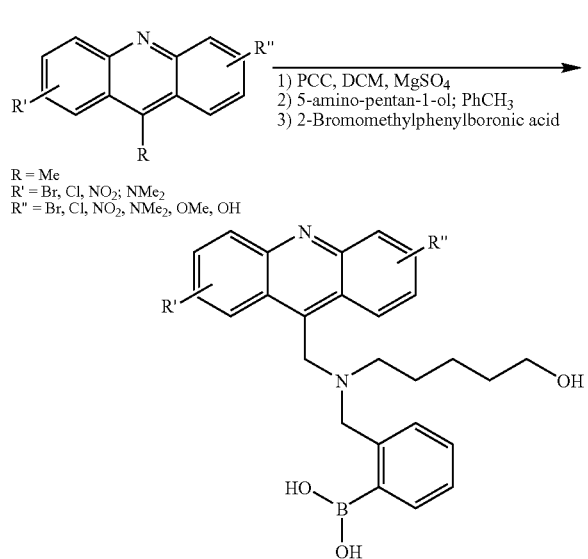

Starting from a halogen (R=Br; Cl) substituted acridine in the 9-position, this fluorophore can be converted to an aldehyde using standard reaction conditions (nBuLi; THF; DMF), although no halogens can be present anywhere else in the ring. Starting with a formyl group (R=CHO) in the 9-position is preferred, however, as this starting fluorophore eliminates some difficult synthetic steps.

However, the acridine-based fluorophore can be further generalized in that at least one heteroatom can be located at other positions within the three-ring structure, rather than at position 10. Some representative fluorophores are shown below. Many of these fluorophores are commercially available. These fluorophores can then be functionalized at a substituent located at the 9-position, as indicated above for the acridine-based biosensor molecules. These preferred substitutents are lower aliphatic groups from 1–4 carbons, an aldehyde, a chloro group, or a bromo group. Using the synthetic methods outlined above for ACRAB and MEACRAB, acridine-like boronate biosensor molecules are reasonably obtained.

Additionally for these flurophore embodiments shown below, the heteroatom may include other atoms as indicated, however, the preferred heteroatoms are nitrogen and sulfur. Moreover, other positions, instead of the 9-position, can be used for further functionalization and synthesis towards the development of acridine-like boronate biosensor molecules. For example, an aldehyde substituent can be located at the 10-position with the heteroatom being located at the position-3 within the three-ring structure. Other variations are also possible, such as a chloro group located at the 7-position and a heteroatom located at the 9-position within the three-ring structure.

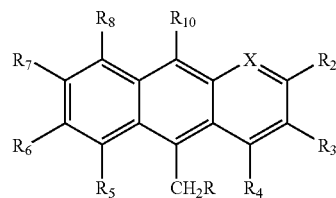

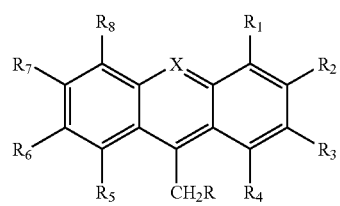

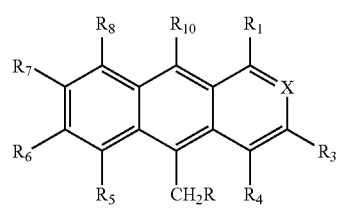

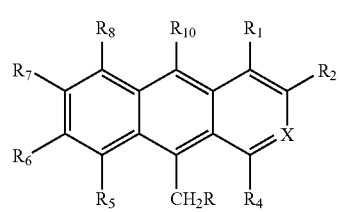

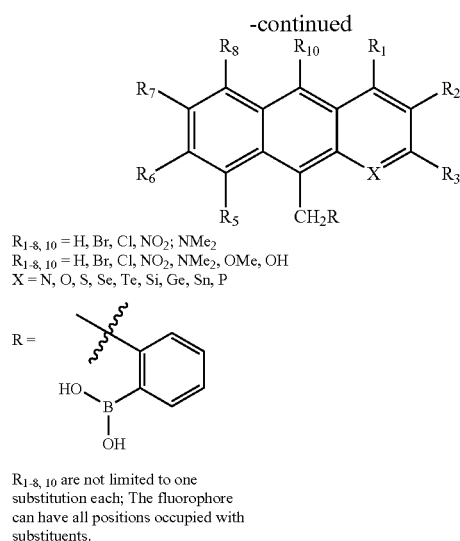

-continued

R$_{1-8, 10}$ = H, Br, Cl, NO$_2$; NMe$_2$
R$_{1-8, 10}$ = H, Br, Cl, NO$_2$, NMe$_2$, OMe, OH
X = N, O, S, Se, Te, Si, Ge, Sn, P

R$_{1-8, 10}$ are not limited to one substitution each; The fluorophore can have all positions occupied with substituents.

Other fluorophore embodiments are acridine-like fluorophores that include two or more heteroatoms, such as phenazines, phenothiazines and phenoxazines. A methylphenazine example is shown below. In this example, the functional group is at the 3-position.

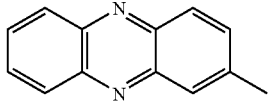

2. Synthetic Methods of Making Embodiments of Acridine-Based Ditopic Boronate Biosensor Molecules of the Invention:

In modeling the binding of glucose to a generalized ditopic acridine-based boronate biosensor molecule it is apparent that the length of the bridging linker should have an effect on the binding interaction. To test this hypothesis, five linkers of various lengths were selected as shown in Table 2.

TABLE 2

Linkers Used in the Production of Acridine-Based Ditopic Boronate Biosensor Molecules

| Linker No. | Linker Name | n Value (number of carbons in linker) |
|---|---|---|
| 1a | Ethylenediamine | 2 |
| 1b | 1,3-diaminopropane | 3 |
| 1c | 1,4-diaminobutane | 4 |
| 1d | 1,5-diaminopentane | 5 |
| 1e | 1,6-diaminohexane | 6 |

These linkers can be used to synthesize generalized acridine-based boronate biosensor molecules of the invention, as depicted in FIG. 4. General, as well as specific, synthetic schemes are given below. The following synthetic methods are predictive of synthetic reactions using acridine-based fluorophores. The following reactions actually have been performed with anthracene-based fluorophores, which are chemically very similar to acridine-based fluorophores used in the present invention, although possessing very different fluorescent properties. The following is a description of these anthracene-based reactions schemes using instead an acridine-based fluorophore, such as acridine-9-carboxyaldehyde. The following reactions, therefore, are based on the notion that this particular change in the fluorophore will yield acridine-based ditopic products, similar to the quantities and purity that have been found for the anthracene-based ditopic products.

a) General Synthetic Schemes

Scheme 1. Synthesis of the Bisacrindine Imines.

Reaction 1 presents a general reaction scheme for the production of a bisacrindine imines. These imines should be freshly prepared since they may not be stable even when stored in the dark at sub-zero degree C. conditions.

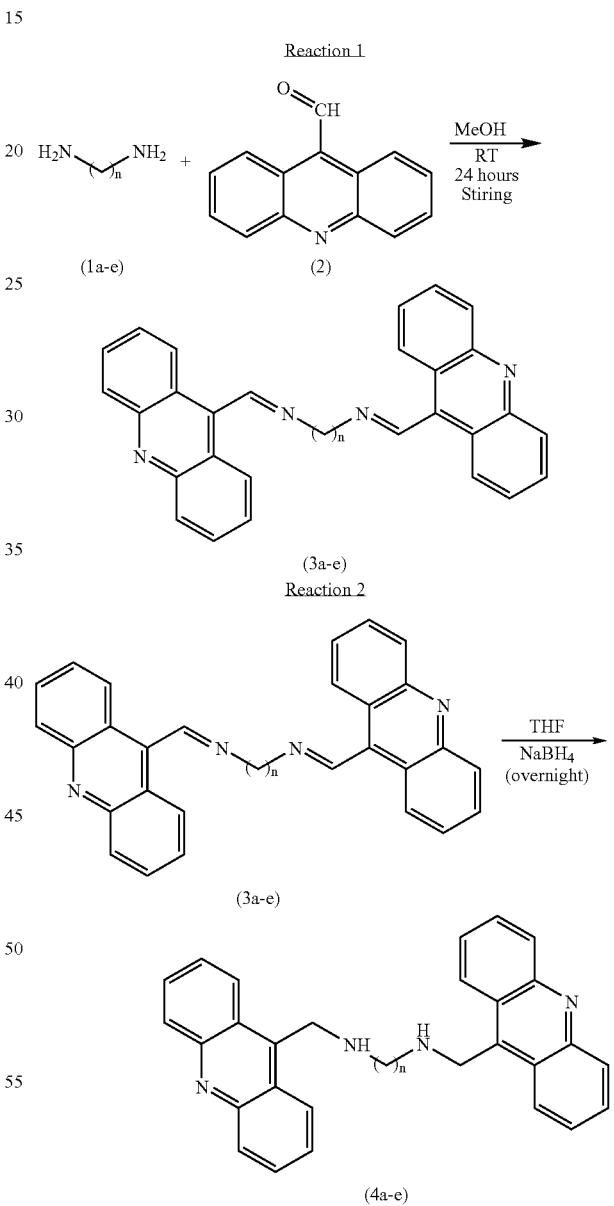

Scheme 2. Generic Reductive Amination Used in all Ditopic Synthesis where n=2,3,4,5,6

This reduction, as illustrated in reaction 2 above, would be carried out using NaBH$_4$ in THF to generally yield a solid product. This product is then alkylated with protected bromo boronic acid to form the ditopic acridine product. This product is either allowed to recrystallize from 4:1 acetonitrile/H$_2$O or hot dimethyl sulfoxide (DMSO).

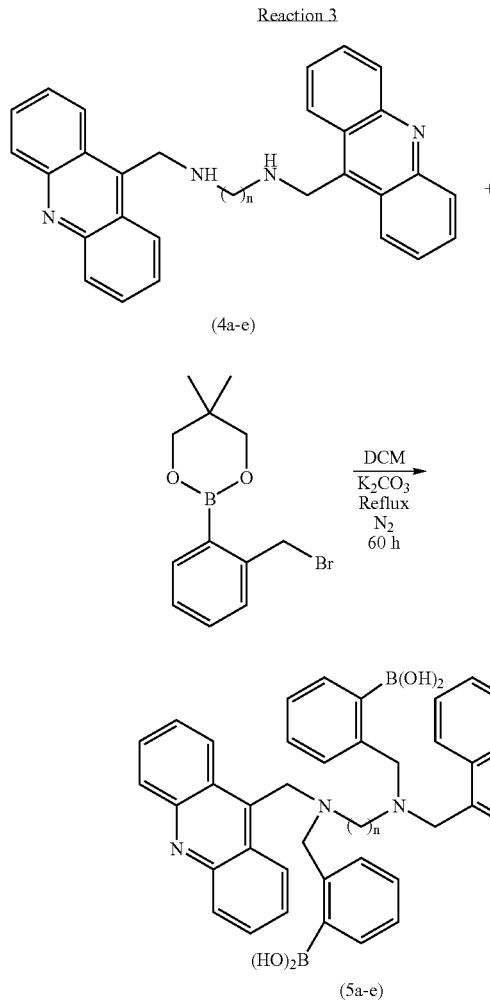

(4a-e)

(5a-e)

Scheme 3. Alkylation of Generic Ditopic

Using the bromo boronic acid-neopentyl glycol ester in the alkylation of the ditopic can be successful, as illustrated in reaction 3 above. For comparable synthesis using an antrhacene fluorophore, rather than an acridine fluorophore, yields were in the 60% range. This alkylation product may be a salt and may require deprotonation. The product can be best purified by recrystallization from 4:1 acetonitrile/H$_2$O or hot dimethyl sulfoxide (DMSO).

b) Specific Synthetic Reactions

All experiments are to be carried out using ACS grade reagents and under nitrogen, unless otherwise specified.

N,N'-Bis-acridin-9-ylmethyl-ethane-1,2-diamine (4a)

The following reactions yield N,N'-Bis-acridin-9-ylmethyl-ethane-1,2-diamine.

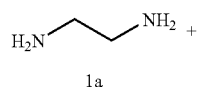

1a

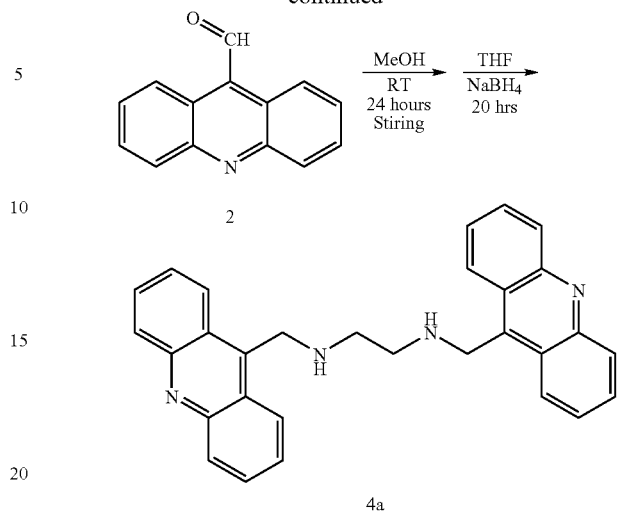

The above reactions should be carried out as follows. To an oven-dried round-bottomed flask equipped with a magnetic stirring bar and a bubbler, 324 μL (4.82×10$^{-3}$ mol) ethylene diamine (1a), 2.198 g (1.06×10$^{-2}$ mol) of acridinecarboxyaldehyde (2) and 100 ml methanol are added. This mixture is allowed to stir overnight. A yellow, pearlescent solid was formed at this step in comparable reactions using anthracene-based molecules. This solid is filtered and washed with methanol until no odor of amine is detectable and the methanol runs clear. This solid is transferred to a dry 200 ml round bottomed flask equipped with a stir bar, a condenser and 100 ml of inhibitor free, anhydrous THF. Sodium borohydride (1.5 g) is added to the reaction vessel and the reaction is heated to reflux for 20 hours. The reaction is cooled to room temperature, poured over 80 ml 1 N HCl, and washed with 100 ml dichloromethane. A solid is formed in the dichloromethane layer, which is filtered and collected. The aqueous layer is made basic. The collected solid from the organic layer is added to the now basic aqueous layer and washed with dichloromethane The dichloromethane layer is dried over MgSO$_4$ and the solvent is removed via rotary evaporation. In comparable reactions with an anthracene fluorophore rather than acridine, the final mass was 0.842 grams (1.911×10$^{-3}$ mol) (79% yield).

N,N'Bis-acridin-9-ylmethyl-N,N'-bis-(2-boronicacid-benzyl)-propane-1,3-diamine (5a)

The following reactions are performed to yield N, N'-Bis-acridin-ylmethyl-N,N'-bis-(2-boronicacid-benzyl)-propane-1,3-diamine.

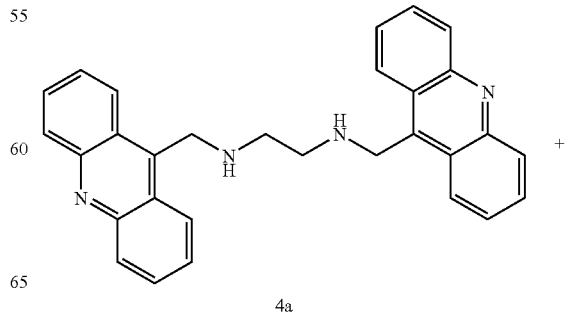

4a

-continued

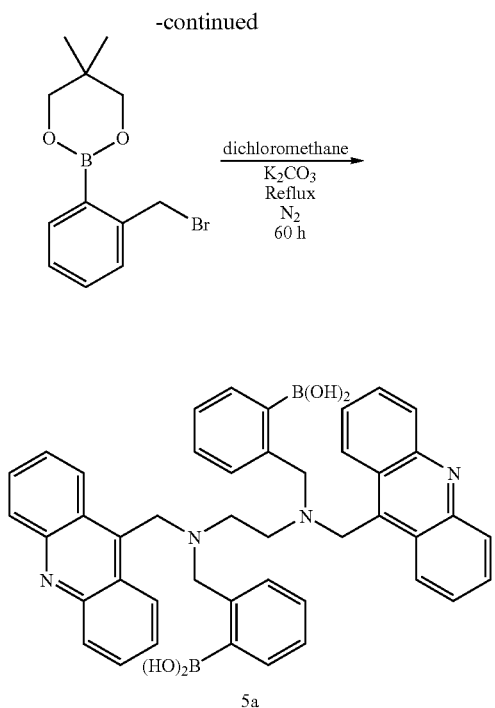

5a

The above reactions should be carried out as follows. To a 200 ml oven-dried round-bottomed flask equipped with a condenser and magnetic stir bar, 300 mg 4a ($6.809\times10^{-4}$ mol), 0.423 g bromoboronic acid ($1.497\times10^{-3}$ mol), 100 ml anhydrous dichloromethane, and 1.5 g potassium carbonate are added. The reaction vessel is heated at reflux for 60 hours. The reaction is allowed to cool to room temperatue and the solid is removed by filtration. This solid is the major product, which is product 5a. The solid is washed with dichloromethane (DCM), methanol, hot water (3×100 ml) and tetrahydrofuran (THF). The product is not soluble in any of these solvents, but the starting materials and potassium carbonate are soluble and thereby removed. The solid is then dissolved in hot DMSO and allowed to recrystallize overnight. This last step is repeated until TLC (5% MeOH in DCM) analysis shows one spot. Usually at least two recrystallizations are required. The yield from this step in comparable syntheses using an anthracene fluorophore rather than acridine is approximately 80% and the product retrieved is a yellow solid.

N,N'-Bis-acridin-ylmethyl-propane-1,3-diamine (4b)

The following reactions yield N,N'-Bis-acridin-ylmethyl-propane-1,3-diamine.

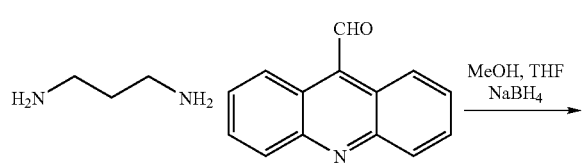

-continued

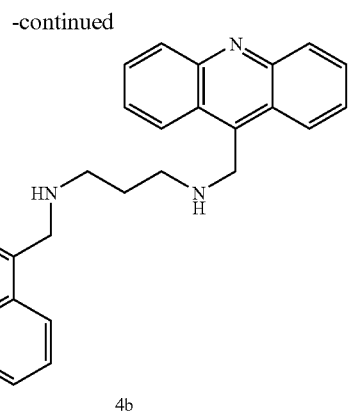

4b

The above reactions should be performed as follows. To a round-bottomed flask containing acrdine-9-carboxyaldehyde (2.06 g, 1.0 mmol) and MeOH (~50 ml), 1,3-diaminopropane (1b) (370 μL, 5 mmol) is added. The reaction is stirred for 1 hr and may be followed by the formation of a yellow precipitate. The precipitate is filtered and washed with cold MeOH. The solid is transferred to a round bottom flask and dissolved in THF (~50 ml). NaBH$_4$ (380, 10 mmol) is added to the reaction and the mixture is stirred for 1 hr. MeOH (~20 ml) is then added to the reaction and the solution is stirred for an additional 1 hr. The reaction is poured onto HCl (1N) and a precipitate should form. The precipitate is filtered and washed with H$_2$O followed by Et$_2$O. In comparable reactions with an anthracene fluorophore rather than acridine, 1.17 g (52% yield) of a pale yellow solid was retrieved.

N,N'Bis-acridin-ylmethyl-N,N'-bis-(2-boronicacid-benzyl)-propane-1,3-diamine (5b)

The following reactions yield N,N'-Bis-acridin-ylmethyl-N,N'-bis-(2-boronicacid-benzyl)-propane-1,3-diamine.

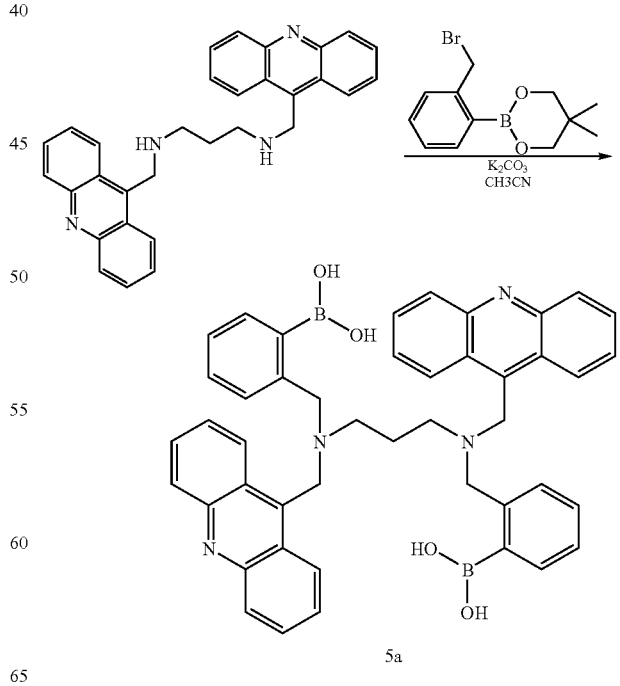

5a

The above reactions should be performed as follows. To a round bottom flask, under argon, K$_2$CO$_3$ (~500 mg), MeCN (~50 ml) and diamine (1.17 g, 2.22 mmol), boronate (1.25 g, 4.44 mmol) are added. The reaction is heated at reflux for 2 days. The reaction mixture is filtered and the filtrate is concentrated to dryness in vacuo. The residue is dissolved in 4:1 ACN:H$_2$O. For comparable reactions with an anthracene-based fluorophore, rather than acridine, yellow crystals were isolated.

N,N'-Bis-acridin-ylmethyl-butane-1,4-diamine (4c)

The following reactions yield N,N'-Bis-acridin-ylmethyl-butane-1,4-diamine.

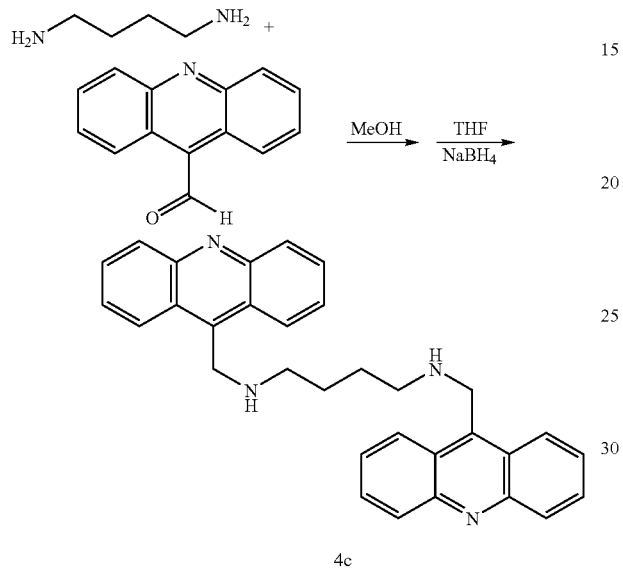

4c

The above reactions should be performed as follows. In an oven dried 200 ml round-bottom flask equipped with a magnetic stir bar and stir plate, acrdine-9-carboxyaldehyde (2.31 g, 0.0112 mol) and MeOH (100 ml, anhydrous) are added. This mixture is allowed to stir under N$_2$ for 5 minutes until a solution is obtained. To this solution, 1,4-diaminobutane (0.500 g, 5.67×10$^{-3}$ mol) is added and allowed to stir for 2 hours until a solid is formed. More MeOH (approximately 50 ml) can be added if the solid prevents proper stirring. This mixture is allowed to run an additional hour until the reaction is confirmed complete by TLC (10% MeOH in DCM) and does not stain positive with ninhydrin. The solid is filtered and washed with portions of MeOH (3×50 ml), until the solid does not smell of amine and the methanol runs colorless. The solid is transferred to a clean, oven-dried flask and anhydrous THF (100 ml) is added. NaBH$_4$ (1.0 g, 26.4 mmol) is added to the reaction by increments of 0.100 g at a time over 2 minutes. Bubbles should slowly develop. This reaction is capped, attached to a bubbler and allowed to react overnight. The reaction is quenched with MeOH (50 ml) and the contents of the reaction vessel are poured over 1 N HCl (80 ml). A solid will precipitate. This solid is filtered and isolated. The reaction mixture is washed with dichloromethane. The aqueous layer is made basic with 1 N NaOH. The resultant solid is filtered and is also reserved for later. For comparable reactions using an anthracene fluorophore rather than acridine, the mass of the "acidic solid" was 1.1 g and was pale yellow in color. The mass of the "basic solid" was 90 mg and was orange in color. An NMR spectrum was taken of both and they were shown to be identical except for a miniscule amount of a contaminant/impurity. The major product is most likely the dichloride salt, since it was not soluble in nearly any solvent, until it was deprotonated with triethylamine (TEA). The molecular weight of the dichloride salt was 541.63 g/mol. Final yield of the comparable anthracene product, rather than acridine, was 1.2 grams (39% yield).

N,N'-Bis-acridin-ylmethyl-N,N'-bis-(2-boronicacid-benzyl-butane-1,4-diamine (5c)

The following reactions yield N,N'-Bis-acridin-ylmethyl-N,N'-bis-(2-boronicacid-benzyl)-butane-1,4-diamine.

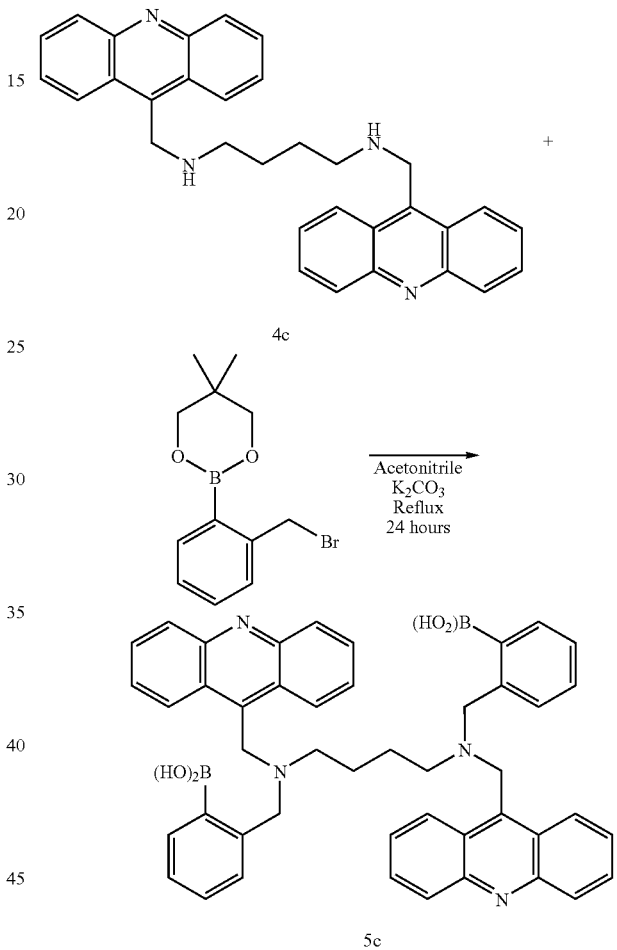

5c

The above reactions should be performed as follows. Into an oven dried round-bottom flask equipped with a magnetic stirrer, a heating mantle and reflux condenser, 100 ml MeCN, 310 mg (6.6×10$^{-4}$ mol) 4c, 0.412 g o-Bromomethyl boronic acid neopentyl glycol ester (1.45×10$^{-3}$ mol) and 1.5 g potassium carbonate (huge excess) are added. This mixture is purged with N$_2$ for ten minutes and allowed to stir overnight. The reaction vessel is then cooled and the resultant solid is filtered. The solid product is recrystallized using hot DMSO or 4:1 acetonitrile/water. In comparable synthetic methods using an anthracene-based fluorophore, rather than an acridine fluorophore, an 80% yield was obtained. Alternatively, DCM is added to the reaction (80 ml) and the reaction is washed with 1N HCl. A precipitate forms in the organic layer and is filtered off and reserved. 1N NaOH is added and a precipitate will form in the organic layer, which should be filtered off and reserved. The organic layer is dried over MgSO$_4$ and the solvent removed via rotary evaporation. In comparable synthetic methods using an anthracene-based fluorophore instead of an acridine, the combined solid fractions had a mass of 212 mg and the NMR revealed that the compound was N,N'-Bis-antharacen-9-ylmethyl-N,N'-bis-(2-boronicacid-benzyl)-butane-1,4-diamine.

N,N'-Bis-anthracen-9-ylmethyl-pentane-1,5-diamine (4d)

The following reaction yields N,N'-Bis-acridin-ylmethyl-pentane-1,5-diamine.

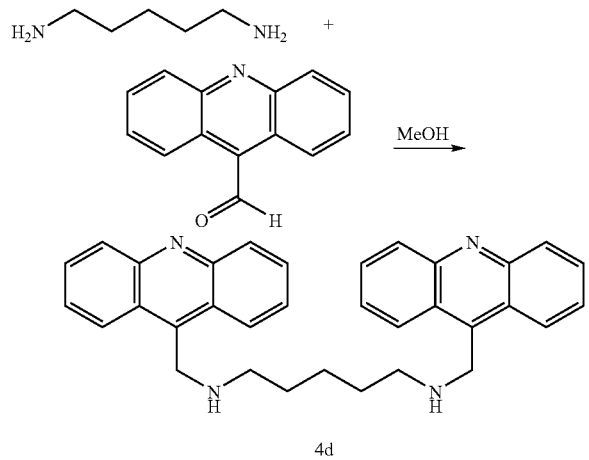

4d

The above reaction is performed as follows. In an oven-dried 200 ml round-bottomed flask equipped with a magnetic stir bar and stir plate, 2.017 g of acridinecarboxyaldehyde (approximately $9.78 \times 10^{-3}$ mol) and 100 ml of MeOH (anhydrous) are added. This mixture is allowed to stir under $N_2$ for 5 minutes until the acridinecarboxyaldehyde is completely dissolved. To this mixture, one part, 0.500 g ($4.89 \times 10^{-3}$ mol) 1,5-diaminopentane is added. This mixture is allowed to stir for 2 hours until a solid is formed. More MeOH can be added (e.g. 50 ml) if the solid prevents proper stirring. This mixture is allowed to stir for an additional hour until the reaction is complete, as confirmed by TLC, and does not stain as a free amine with ninhydrin. The resultant solid is filtered and washed with 3×50 ml portions of MeOH until the solid does not smell of amine and the methanol runs colorless. The solid is then transferred to a clean, oven-dried flask and 100 ml anhydrous THF is added. The solid may be insoluble. Approximately 1.0 g of $NaBH_4$ is added to the reaction. This reaction is allowed to react overnight, with proper venting (via a bubbler). The reaction is quenched with 50 ml MeOH and the contents of the reaction vessel are poured over 80 ml 1 N HCl. A solid will precipitate, which is to be filtered off and reserved for later. The reaction is then washed with DCM (the organic portion is to be saved) and then made basic with 1 N NaOH. Another solid will precipitate and also should be filtered off and reserved for later. In comparable reactions with an anthracene fluorophore rather than acridine, the mass of the acidic solid was 1.32 g and the mass of the basic solid was 75 mg. An NMR was taken of these solids, which showed them to be identical. These solids were deprotonated via partitioning between NaOH/DCM wash and then dissolved in DCM. The final yield was 1.40 grams or $2.89 \times 10^{-3}$ mol (60% yield).

N,N'-Bis-acridin-ylmethyl-N,N'-bis-(2-boronic acid-benzyl)-pentane-1,5-diamine (5d)

The following reactions yield N,N'-Bis-acridin-ylmethyl-butane-1,4-diamine.

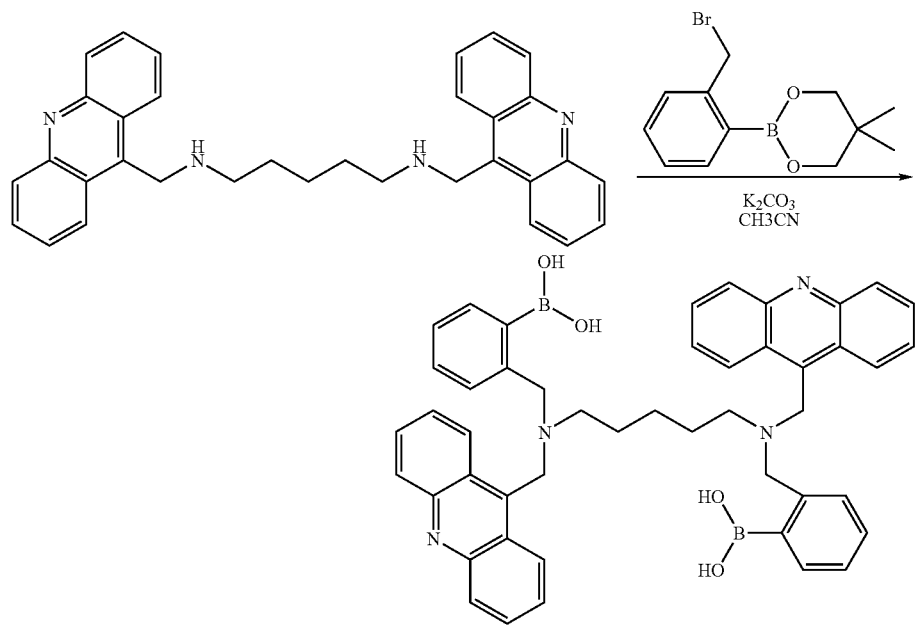

5d

The above reactions should be performed as follows. Into an oven-dried round-bottomed flask equipped with a magnetic stirrer, a heating mantle, and reflux condenser, 100 ml MeCN, 300 mg ($6.21 \times 10^{-4}$ mol) 4d, 0.386 g o-bromomethylphenylboronic acid neopentyl glycol ester ($1.36 \times 10^{-3}$ mol) and 1.5 g potassium carbonate are placed. This mixture is purged with $N_2$ for ten minutes, heated to reflux, and allowed to react overnight with constant stirring. The reaction vessel is then cooled and the resultant solid is filtered. The solid is then recrystallized in hot DMSO or 4:1 acetonitrile/water. The solid product can be obtained in an approximate 80% yield using comparable synthetic methods with an anthracene-based fluorophore rather than an acridine-based fluorophore. Alternatively, DCM is added to the solid (80 ml) and the reaction is washed with 1N HCl. A precipitate will form in the organic layer, which is to be filtered off and reserved. 1N NaOH is added. A precipitate will form in the organic layer that is to be filtered off and reserved. The organic layer is then dried over $MgSO_4$ and the solvent removed via rotary evaporation. The resultant solid is compared via TLC with two other fractions and the product in the organic layer. In the case of anthracene-based reactions rather than acridine, the organic layer was too impure to use, however, the combined solid fractions had a mass of 212 mg.

N,N'-Bis-acridin-ylmethyl-hexane-1,6-diamine (4e)

The following reactions yield N,N'-Bis-acridin-ylmethyl-hexane-1,6-diamine.

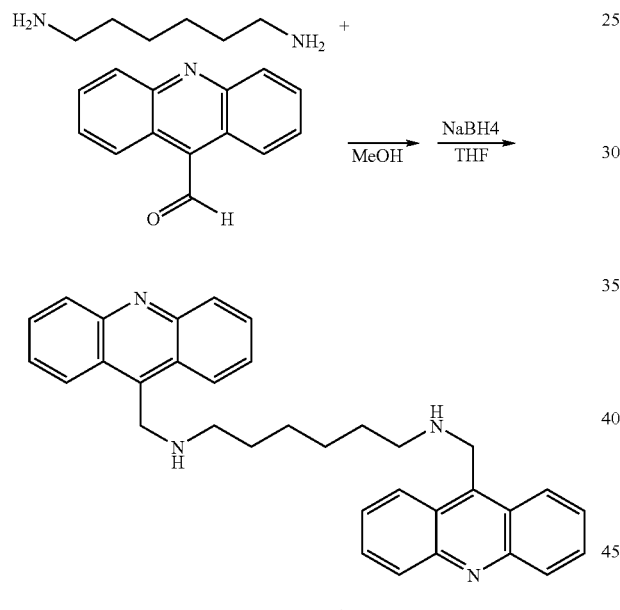

4e

The above reactions should be performed as follows. In an oven-dried 200 ml round-bottomed flask equipped with a magnetic stir bar and stir plate, 3.91 g of acridinecarboxyaldehyde (approximately $9.78 \times 10^{-3}$ mol) and 100 ml MeOH (anhydrous) are added. This mixture is allowed to stir under $N_2$ for 5 minutes until the acridinecarboxyaldehyde is completely dissolved. To this mixture is added 1.00 g ($8.605 \times 10^{-3}$ mol) 1,6-hexane diamine in one portion. This mixture is allowed to stir for 2 hours until a solid is formed. More MeOH can be added (e.g., 50 ml) if the solid prevents proper stirring. This mixture is allowed to run an additional hour until the reaction is confirmed complete by TLC and does not stain as a free amine with ninhydrin. The solid is then filtered off and washed with MeOH (3×50 ml) until the solid does not smell of amine and the methanol runs colorless. The solid is transferred to a clean, oven-dried flask and 100 ml anhydrous THF is added. The resultant solid may be insoluble. If so, approximately 1.0 g $NaBH_4$ is to the reaction mixture. This reaction is capped, attached to a bubbler and allowed to stir overnight. The reaction is quenched with 50 ml of MeOH and the contents of the reaction vessel are poured over 80 ml 1 N HCl. A solid will precipitate, and should be filtered off and reserved for later. The reaction is then washed with DCM (the organic portion is to be saved) and then made basic with 1 N NaOH. Another solid will precipatate and should be filtered off, and reserved for later. The solid is deprotonated via partitioning between NaOH and DCM. From comparable reactions with an anthracene fluorophore rather than acridine, the mass of the acidic solid was 2.23 g and the mass of the basic solid was 199 mg. A confirmatory NMR was taken of the free base. The final yield was 2.42 grams or $5.01 \times 10^{-3}$ mol (60% yield).

N,N'-Bis-acridin-ylmethyl-N,N'-bis-(2-boronic acid-benzyl)-hexane-1,6-diamine (5e)

The following reactions yield N,N'-Bis-acridin-ylmethyl-N,N'-bis-(2-boronic acid-benzyl)-hexane-1,6-diamine.

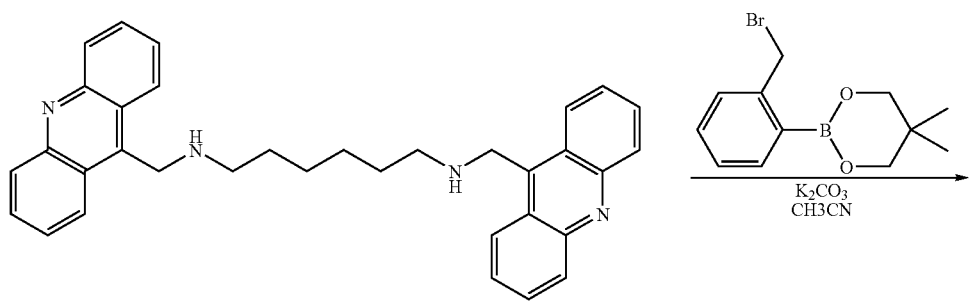

4e

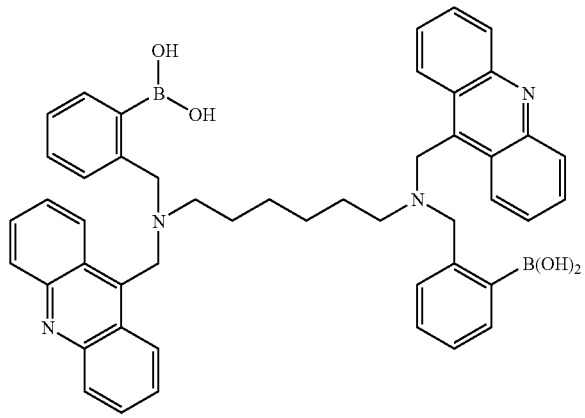

5e

The above reactions should be performed as follows. Into an oven-dried round-bottomed flask equipped with a magnetic stirrer, a heating mantle, and reflux condenser, 100 ml MeCN, 0.843 mg (1.697×10$^{-3}$ mol) 4e, 1.039 g o-bromomethyl boronic acid neopentyl glycol ester (3.56×10$^{-3}$ mol) and 1.5 g potassium carbonate are added. The flask is purged with N$_2$ for ten minutes, heated to reflux overnight with constant stirring. The reaction vessel is then cooled and the solid is filtered. The solid is then recrystallized using hot DMSO or 4:1 acetonitrile/water. The solid product can be obtained in an approximate 80% yield using comparable these synthetic methods with an anthracene-based fluorophore rather than an acridine-based fluorophore. Alternatively, DCM is added to the reaction (80 ml) and the reaction is washed with 1N HCl. A precipitate in organic layer will form and is to be filtered off and reserved. 1N NaOH addition results in a precipitate being formed in organic layer, which should be filtered off and reserved. In comparable reactions with an anthracene fluorophore rather than acridine, the combined solid fractions had a mass of 812 mg or 1.06×10$^{-3}$ mol (62% yield).

Other Ditopic Molecules:

The above examples of ditopic acridine-based boronate biosensor molecules are not to be limited by the specific linkers utilized. Other embodiments with alternative linker are also envisioned. The use of alternative linkers can be utilized to further optimize the positioning of the glucose recognition moieties in ditopic acridine-based boronate biosensor molecules, so as to fine-tune the sensitivity of these molecules to glucose and to facilitate the incorporation of ditopic molecules into a polymer.

3. Fluorescence Studies of Embodiments of the Acridine-Based Boronate Biosensor Molecules of the Invention a) Monotopic Biosensor Molecules Glucose transduction of particular acridine-based boronate bio sensor molecules was observed using fluorescence spectroscopy. Fluorescence measurements were taken on a Yorbin Fluorolog instrument. In the following experiments glucose measurements were verified using a YSI (Colorado Springs) analyzer at 25 deg C., in phosphate buffer saline (PBS), pH 7.4, containing 0.5% DMSO.

A sample of ACRAB was diluted in PBS (Phosphate Buffered Saline, pH 7.4) containing 0.5% DMSO until an approximate value of 10 µM ACRAB was obtained. Aliquots of glucose were added and responses were measured at 436 nm, or maximum intensity. (See Table 3). As can be observed from inspection of Table 3, a 41% increase in transduction was observed at approximately 200 mg/dL glucose.

TABLE 3

Fluorescence Measurements of ACRAB with Glucose at 436 nm

| Aliquot | Intensity (cps × 10$^3$) | Glucose (mg/dL) | Transduction (%) |
|---|---|---|---|
| 0 | 260.2 | 0 | N/A |
| 1 | 298.7 | 50 | 15 |
| 2 | 329.5 | 150 | 27 |
| 3 | 368 | 200 | 41 |
| 4 | 384.4 | 300 | 48 |

Another transduction experiment was performed with ACRAB at 500 nm, or approximately 25% of the value of maximum intensity. These results are shown in Table 4. The data taken at 500 nm generally parallel those taken at 436 nm, thus indicating no decrease in performance of the acridine-based boronate biosensor molecule at the longer wavelength. This shift of 83 nm is very significant in that it provides about a 10-fold increase of transmission of light through tissue and skin.

TABLE 4

Fluorescence Measurements of ACRAB with Glucose at 500 nm.

| Aliquot | Intensity (cps × 10$^3$) | Glucose (mg/dL) | Transduction (%) |
|---|---|---|---|
| 0 | 98.4 | 0 | N/A |
| 1 | 109.5 | 49 | 11 |
| 2 | 122.0 | 149 | 24 |
| 3 | 134.8 | 198 | 37 |
| 4 | 144.8 | 284 | 47 |
| 5 | 153.9 | 374 | 56 |
| 6 | 159.7 | 441 | 62 |
| 7 | 164.7 | 559 | 67 |

A sample of MEACRAB was then tested for its ability to fluoresce in the presence of glucose. The first experiment involved observing transduction (or fluorescence) at 500 nm (25% of $I_{max}$@438 nm). MEACRAB was slightly less soluble than ACRAB, thus 4% DMSO was needed to solubilize the material in PBS at a concentration of 10 μM. The results are presented in Table 5.

TABLE 5

Fluorescence Measurements of MEACRAB with Glucose at 500 nm.

| Aliquot | Intensity (cps × 10³) | Glucose (mg/dL) | Transduction (%) |
|---|---|---|---|
| 0 | 100 | 0 | N/A |
| 1 | 130 | 93 | 30 |
| 2 | 160 | 184 | 60 |
| 3 | 200 | 275 | 100 |
| 4 | 220 | 364 | 120 |
| 5 | 270 | 459 | 170 |
| 6 | 290 | 547 | 190 |
| 7 | 320 | 650 | 220 |

Figure 13:
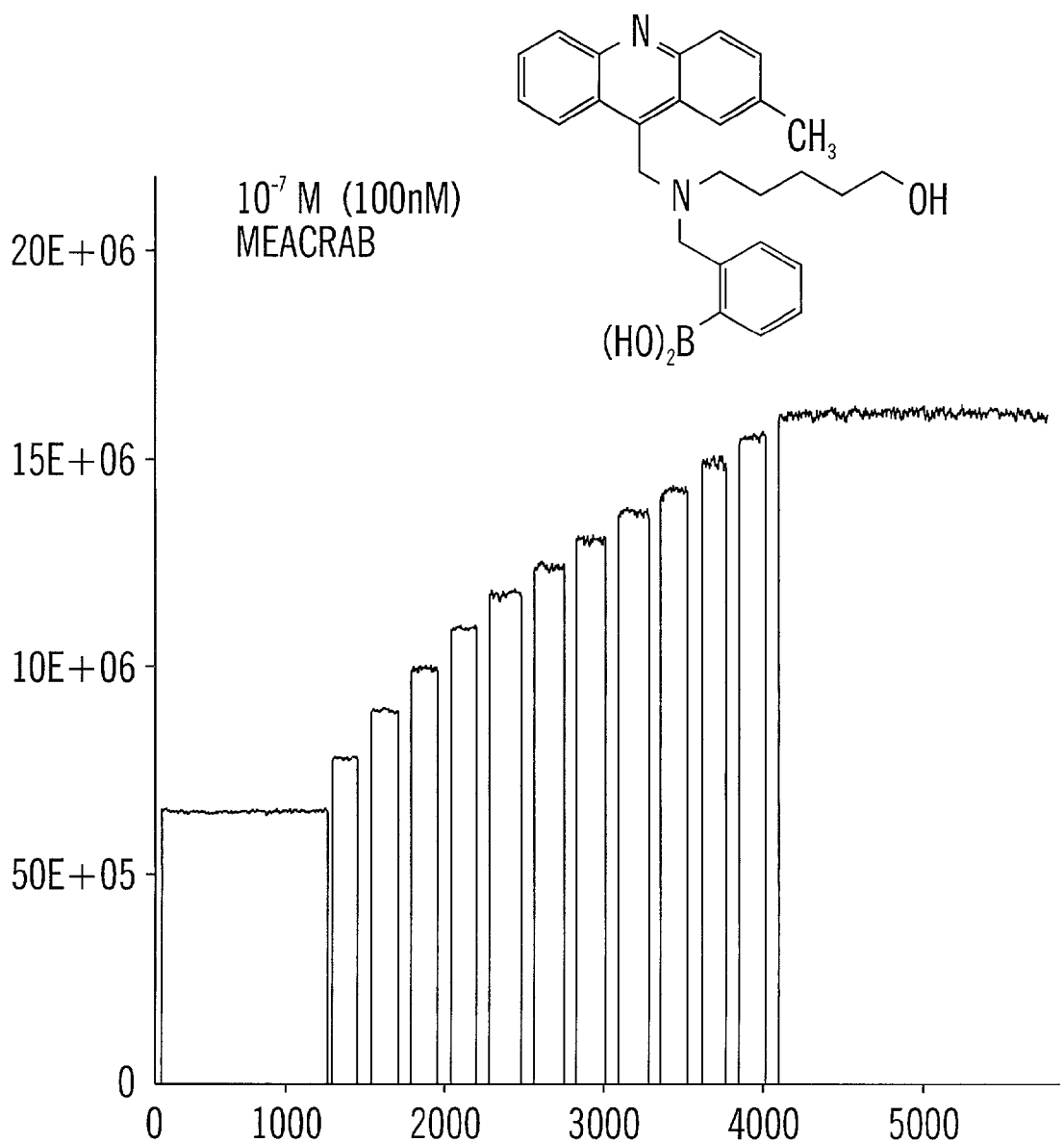
FIG. 13 is a timescan showing the changes in fluorescence of the methylacridine boronate biosensor molecule ($10^{-7}$ M) with increasing glucose concentrations from approximately 0 to 1000 mg/dl.

MEACRAB was then diluted 100-fold to 100 nM and transduction at conditions of ambient temperature. The solution contained 0.5% DMSO. The results are presented in Table 5. MEACRAB performed better at 100 nM at an emission wavelength of 500 nm than ACRAB, or MEACRAB itself, at 10 μM, as it appeared to be more soluble in an aqueous solution and have greater molar efficiency. A fluorescence timescan of the results in Table 6 is given in FIG. 13.

TABLE 6

Fluorescence Measurements of MEACRAB with Glucose at 509 nm

| Aliquot | Intensity (cps × 10⁴) | Glucose (mg/dL) | Transduction (%) |
|---|---|---|---|
| 0 | 62 | 0 | N/A |
| 1 | 75 | 87 | 21 |
| 2 | 80 | 173 | 29 |
| 3 | 95 | 256 | 53 |
| 4 | 110 | 341 | 77 |
| 5 | 120 | 425 | 94 |
| 6 | 130 | 510 | 109 |
| 7 | 135 | 603 | 118 |
| 8 | 137 | 683 | 121 |
| 9 | 140 | 767 | 126 |
| 10 | 145 | 834 | 134 |
| 11 | 150 | 927 | 142 |
| 12 | 160 | 1012 | 158 |

CONCLUSION

The ACRAB and MEACRAB embodiments of the acridine-based boronate bio sensor molecules in accordance with embodiments of the invention are good transducers molecules as they are capable of effectively reporting on ambient glucose concentrations. Moreover, these embodiments can be interrogated at wavelengths up to about 500 nm. Further, the MEACRAB biosensor molecule can effectively transduce in the nanomolar range, thus yielding a biosensor molecule with both long wavelength capacity and high efficiencies of transduction.

b) Ditopic Biosensor Molecules

The following transduction experiment can be conducted with an ethyl ditopic acridine-based boronate biosensor molecule (1a). For the anthracene-based ditopic biosensor molecule, the following results, shown in Table 7, were obtained.

TABLE 7

Transduction Experiment with an Ethyl Ditopic

| Ditopic concentration | Glucose Concentration (mg/dL) | Intensity CPS (× 10⁴) | Transduction (%) |
|---|---|---|---|
| 0.24 mM | 0 | 80 | 0 |
| 0.24 mM | 6.8 | 91 | 13 |
| 0.24 mM | 13.0 | 100 | 25 |
| 0.24 mM | 19.2 | 101 | 26 |

For this experiment, a solution of (5a) (0.850 mg in 100 ml DMSO) is prepared and 0.100 ml of this solution is diluted to 50.00 ml in PBS. Of this PBS solution, 3.0 ml is pushed through a 0.2-micron syringe filter into a cuvette for fluorescence testing. For comparable experiments with an ethyl-bridged bisanthracenyl ditopic biosensor molecule, as shown in Table 7, the fluorescence results showed transduction in the 6.8–19.2 mg/dL range. These experiments were carried out under the following conditions: $\lambda_{excitation}$=352 nm; $\lambda_{emission}$=415 nm.

The foregoing written description is considered to be sufficient to enable one skilled in the art to practice the invention. Further, the present invention is not to be limited in scope by the examples presented herein. Indeed, various modifications to the present invention, in addition to those shown and described herein will become apparent to those skilled in the art from the foregoing description and fall within the scope of the appended claims.

What is claimed is:

1. A biosensor molecule, the biosensor molecule comprising:
   an acridine-based fluorophore;
   a boronate binding moiety that is capable of specifically and reversibly binding a polyhydroxylate analyte in a sample; and
   a linker moiety that links the fluorophore to the boronate binding moiety, wherein the biosensor molecule is capable of emitting a light signal in the visible to near infrared region of the spectrum that can be correlated to a polyhydroxylate analyte concentration in a sample and further wherein the biosensor molecule comprises a molecule of the formula:

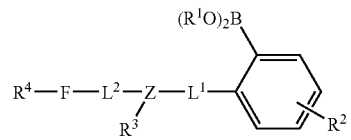

wherein:
   F is an acridine-based fluorophore;
   $R^1$ is selected from the group consisting of hydrogen, aliphatic and aromatic moieties;
   $R^2$ and $R^4$ are optional moieties selected from the group consisting of hydrogen, aliphatic and aromatic moieties and groups that are capable of forming covalent bonds to a biocompatible matrix;
   $L^1$ and $L^2$ are —CH$_2$—;
   Z is nitrogen;
   $R^3$ is an optional group selected from the group consisting of hydrogen, aliphatic and aromatic moieties and groups that are capable of forming covalent bonds to a biocompatible matrix; and wherein F and Z are capable of being involved in an intramolecular photo-induced electron transfer process that quenches the fluorescence of F in the absence of bound polyhydroxylate analyte.

2. The biosensor molecule of claim 1, wherein the biosensor molecule emits light at about 500 nm or longer.

3. The biosensor molecule of claim 1, wherein the polyhydroxylate analyte is glucose.

4. The biosensor molecule of claim 1, wherein the acridine-based boronate biosensor molecule has at least one maximum wavelength in an emission spectrum of the biosensor molecule which is greater than about 420 nm.

5. The biosensor molecule of claim 4, wherein the acridine-based boronate biosensor molecule has at least one emission wavelength that is greater than about 450 nm with an intensity that is at least 25 percent of the intensity of a wavelength of a maximum intensity in the emission spectrum.

6. The biosensor molecule of claim 1, wherein the acridine-based boronate biosensor molecule is attached to a polymer matrix.

7. The biosensor molecule of claim 1, wherein the acridine-based fluorophore has at least one maximum wavelength in an emission spectrum of the biosensor which is between about 420 nm and about 750 nm.

8. The biosensor molecule of claim 1, wherein the acridine-based fluorophore is acridine orange.

9. The biosensor molecule of claim 2, wherein $R^3$ includes a hydroxyl or an amine functional group.

10. The biosensor molecule of claim 9, wherein the hydroxyl or amine functional group includes an aliphatic linker with 2 or more carbon atoms.

11. The biosensor molecule of claim 1, wherein the acridine-based fluorophore further includes one or more moieties selected from the group consisting of at least an aliphatic group, an aromatic group, a haloalkane, an alcohol, an ether, an amine, an aldehyde, a ketone, an ester, a carboxylic acid, a sulfonic acid, a cyano group and a phosphoric acid.

12. An acridine-based fluorescent biosensor system for measuring in-vivo levels of a polyhydroxylate analyte, the biosensor system comprising:

the acridine-based fluorescent biosensor molecule of claim 1 attached to, or contained within, a polymer matrix to form the biosensor of the biosensor system;

an optical light source; and a detector which detects a fluorescent signal, wherein the signal correlates to the in-vivo levels of the polyhydroxylate analyte.

13. An implantable biosensor, the biosensor comprising the acridine-based biosensor molecule of claim 1 contained in a polymer matrix.

14. The implantable biosensor of claim 13, wherein the polymer matrix is biocompatible and water-soluble.

15. The implantable biosensor of claim 14, wherein the water-soluble polymer matrix is selected from polyethylene glycol (amino-terminated), polyethylene glycol (hydroxy terminated), Jeffamine polymers (2-propyl amino terminated block-polypropylene oxide block-polyethylene oxide block-polypropylene oxide), poly(vinyl alcohol), poly (acrylic acid), and mixtures of these polymers.

16. The implantable biosensor of claim 13, wherein the biosensor is contained in a biocompatible, water-insoluble material that is permeable to the polyhydroxylate analyte.

17. The biosensor of claim 16, wherein the water-insoluble material is selected from polyesters of carbonic acid, poly(vinylchloride), polyamides, polychloroethers, poly(urethanes), poly(imides) and mixtures of these materials.

18. The biosensor of claim 13, wherein the polymer matrix is a multiple attachment-point polymer.

19. The biosensor of claim 18, wherein the multiple attachment-point polymer is selected from at least cross-linked poly(vinyl alcohol), cross-linked poly(acrylic acid), star dendrimers and mixtures of these polymers.

20. The biosensor of claim 13, wherein the polymer matrix is polycarboxystyrene.

21. The biosensor of claim 13, wherein the polymer matrix includes a blend of polymers selected to affect the pH and/or solubility of the environmental milieu surrounding the acridine-based biosensor molecule.

\* \* \* \* \*